US010653303B2

(12) United States Patent
Asaoka et al.

(10) Patent No.: US 10,653,303 B2
(45) Date of Patent: May 19, 2020

(54) ENDOSCOPE AND HARDNESS ADJUSTMENT DEVICE

(71) Applicant: FUJIFILM Corporation, Tokyo (JP)

(72) Inventors: Takuro Asaoka, Kanagawa (JP); Yoshihiro Ueda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 730 days.

(21) Appl. No.: 15/345,477

(22) Filed: Nov. 7, 2016

(65) Prior Publication Data

US 2017/0127910 A1    May 11, 2017

(30) Foreign Application Priority Data

Nov. 9, 2015  (JP) ................. 2015-219209

(51) Int. Cl.
*A61B 1/00* (2006.01)
*A61B 1/005* (2006.01)

(52) U.S. Cl.
CPC .......... *A61B 1/0052* (2013.01); *A61B 1/0055* (2013.01); *A61B 1/0057* (2013.01)

(58) Field of Classification Search
CPC .... A61B 1/0052; A61B 1/0055; A61B 1/0057
USPC .................................. 600/144, 149
See application file for complete search history.

(56) References Cited

U.S. PATENT DOCUMENTS

| | | | | |
|---|---|---|---|---|
| 5,179,935 A * | 1/1993 | Miyagi | ................. | A61B 1/0055 600/108 |
| 5,885,208 A * | 3/1999 | Moriyama | ......... | A61B 1/00078 600/144 |
| 6,203,494 B1 * | 3/2001 | Moriyama | ........... | A61B 1/0052 600/144 |
| 8,366,606 B2 * | 2/2013 | Watanabe | .......... | A61B 1/00071 600/104 |
| 8,702,595 B2 * | 4/2014 | Ueki | ..................... | A61B 1/0052 600/144 |
| 9,089,259 B2 * | 7/2015 | Takeuchi | ............. | A61B 1/0051 |
| 2015/0087905 A1 * | 3/2015 | Ueda | .................. | A61B 1/00078 600/109 |

FOREIGN PATENT DOCUMENTS

| | | |
|---|---|---|
| JP | S49-065086 | 6/1974 |
| JP | 2002253476 | 9/2002 |
| JP | 3614986 | 1/2005 |

OTHER PUBLICATIONS

"Office Action of Europe Counterpart Application", dated Dec. 20, 2018, p. 1-p. 4.
"Search Report of Europe Counterpart Application", dated Mar. 21, 2017, p. 1-p. 9.

* cited by examiner

*Primary Examiner* — Alexandra L Newton
*Assistant Examiner* — Rynae Boler
(74) *Attorney, Agent, or Firm* — JCIPRNET

(57) ABSTRACT

Provided are an endoscope and a hardness adjustment device configured so that an arrangement space of built-in components in an operation portion can be ensured and that burden on a coil spring and a wire can be reduced. In an operation portion, a retained portion of a coil spring unit is retained at a first radial position by a coil spring holder as a first retainer, and a base end portion of a wire unit is retained at a second radial position by a wire holder as a second retainer. A base end portion of the coil spring unit is retained at a third radial position by a coil spring contact portion as a third retainer.

13 Claims, 20 Drawing Sheets

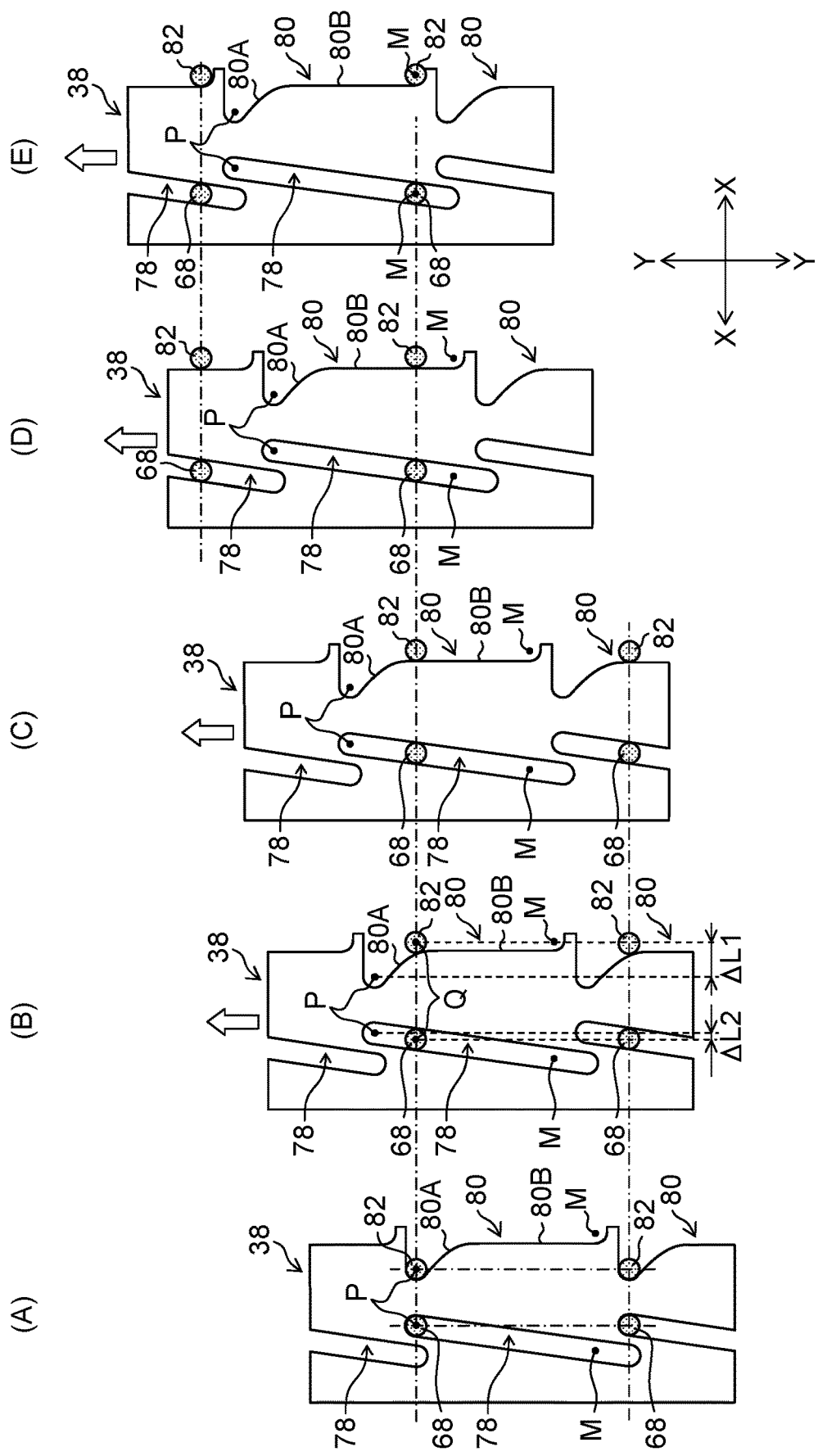

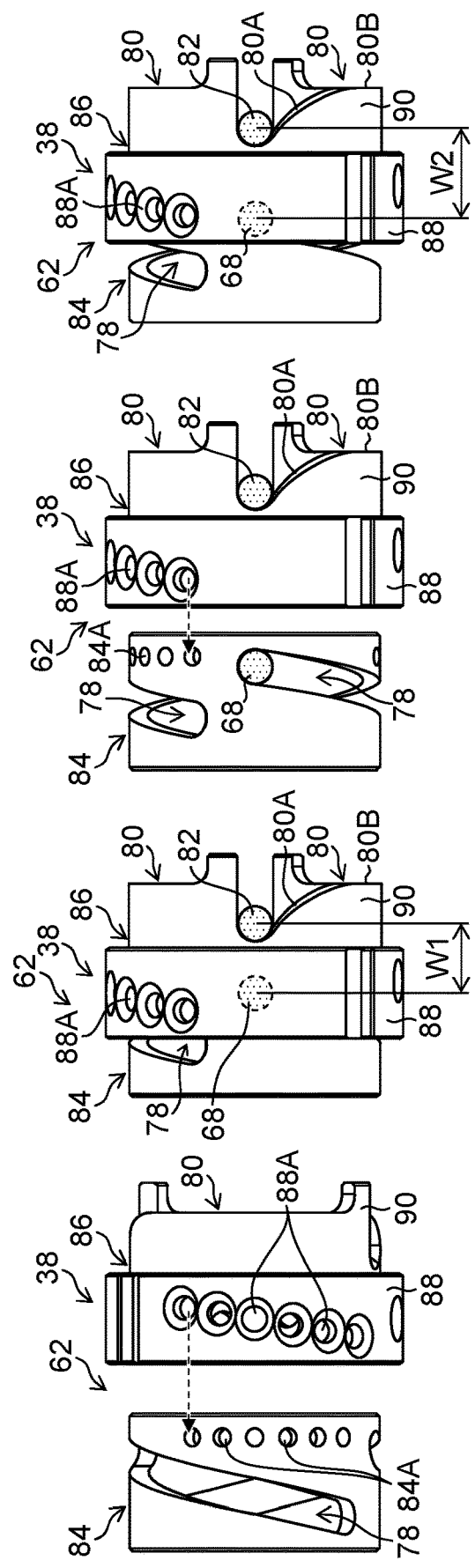

ENDOSCOPE AND HARDNESS ADJUSTMENT DEVICE

CROSS-REFERENCE TO RELATED APPLICATIONS

The present application claims priority under 35 U.S.C. § 119 to Japanese Patent Application No. 2015-219209, filed on Nov. 9, 2015. The above application is hereby expressly incorporated by reference, in its entirety, into the present application.

BACKGROUND OF THE INVENTION

Field of the Invention

The present invention relates to an endoscope and a hardness adjustment device, and particularly relates to an endoscope and a hardness adjustment devise capable of adjusting the hardness of a flexible portion of the endoscope.

Description of the Related Art

Typically, medical diagnosis utilizing an endoscope has been broadly performed in a medical field. In particular, an image in a body cavity is acquired by an endoscope configured such that an image pickup element such as a charge coupled device (CCD) is embedded in a tip end portion of an endoscope insertion portion to be inserted into the body cavity. Signal processing is performed for such an image by a processor device, and then, the image is displayed on a monitor. A doctor observes the displayed image for the purpose of diagnosis, or inserts a treatment tool through a treatment tool insertion channel to perform the procedure for collecting a sample or cutting a polyp, for example.

Generally, an endoscope is substantially configured such that an operation portion to be grasped and operated by a practitioner and an insertion portion to be inserted into a body cavity etc. are continuously provided and that a universal cable for connection to a connector portion etc. is drawn from the operation portion. The universal cable protrudes from the operation portion, and the other end portion of the universal cable is detachably connected to an optical source device or a processor device.

The insertion portion of the endoscope includes a flexible portion having flexibility so that the insertion portion can be also inserted into a complicated curved insertion path. However, a tip-end-side direction of the insertion portion is not fixed due to the flexibility, leading to a problem that it is difficult to insert the insertion portion in a target direction. Moreover, in order to perform certain procedure or observation, the insertion portion might sometimes need to be fixed in a shape when the insertion portion has been inserted into the body cavity.

For these reasons, an endoscope configured such that a coil spring (a helical spring) and a hardness adjustment unit including a wire inserted into the coil spring are arranged in a flexible portion (a flexible tube portion) has been disclosed in Japanese Patent Application Laid-Open No. 49-65086. According to the endoscope of Japanese Patent Application Laid-Open No. 49-65086, a practitioner operates an operation ring provided at an operation portion to compress the coil spring in the axial direction thereof, thereby increasing the degree of flexibility (the hardness) of the flexible tube portion.

In the endoscope of Japanese Patent Application Laid-Open No. 49-65086, a wire fixing portion to which a base end portion of the wire is fixed is provided in the operation portion. Moreover, a rotary ring provided with a helicoid groove is provided in the operation portion, a mover being fixed to a base end portion of the coil spring and being inserted into the helicoid groove. This rotary ring is rotatably operated by the operation ring. That is, a fitting portion in which the mover is fitted into the helicoid groove and the above-described wire fixing portion are provided in the operation portion. Moreover, in the endoscope of Japanese Patent Application Laid-Open No. 49-65086, the wire fixing portion and the fitting portion are arranged on an extension of the coil spring along the axial direction of the coil spring.

SUMMARY OF THE INVENTION

A plurality of well-known built-in components such as a treatment tool insertion channel, a curving operation wire, an air/water supply conduit, a light guide including an optical fiber bundle, and a signal line are arranged in the operation portion and an insertion portion. Moreover, the inner diameter of the operation portion is typically larger than that of the insertion portion.

When the wire fixing portion and the fitting portion are arranged on the extension of the coil spring along the axial direction of the coil spring in the endoscope with the above-described configuration, the wire fixing portion is, in a radial direction, apart from an inner wall surface of the operation portion toward the center axis of the operation portion. For this reason, the wire fixing portion needs to be provided at a tip end of a metal fitting, such as a bracket, protruding from the inner wall surface of the operation portion toward the center axis of the operation portion. Moreover, a rotary ring having a diameter much smaller than the inner diameter of the operation portion needs to be used at the fitting portion.

However, since the plurality of built-in components are arranged in the operation portion, protrusion of the metal fitting in the operation portion and arrangement of the small-diameter rotary ring lead to problems that the metal fitting and the small-diameter rotary ring provide limitations on an arrangement space of the built-in components and that the built-in components are damaged by the metal fitting and the small-diameter rotary ring.

In order to solve the above-described problems, when the wire fixing portion and the fitting portion are provided close to the inner wall surface of the operation portion, the coil spring linearly disposed along the insertion portion is bent outward (in the direction opposite to the direction toward the inner diameter center of the operation portion) at a connection portion between the insertion portion and the operation portion. That is, the axis of the coil spring disposed at the operation portion inclines with respect to the axis of the coil spring disposed at the insertion portion.

When the coil spring in the above-described form is compressed by the operation ring, the inclination angle of the axis of the coil spring disposed at the operation portion with respect to the axis of the coil spring disposed at the insertion portion sharply increases. That is, the coil spring is sharply bent in the operation portion when the coil spring is compressed, and as a result, the coil spring might be buckled due to burden on the coil spring. In this case, it is difficult to compress the entirety of the coil spring, and for this reason, there is a problem that the degree of flexibility of the flexible tube portion cannot be sufficiently changed. Similarly, the wire is also greatly bent in the operation portion, leading to a problem that burden is also provided on the wire.

The present invention has been made in view of the above-described situation, and is intended to provide an endoscope and a hardness adjustment device configured so that an arrangement space of built-in components in an operation portion can be ensured and that burden on a coil spring and a wire can be reduced.

In order to accomplish the above-described goal, the endoscope of the present invention includes an insertion portion including a flexible portion, an operation portion provided continuously to a base end side of the insertion portion, a coil spring unit including a coil spring provided to extend from the flexible portion to the operation portion, a wire unit provided to extend from the flexible portion to the operation portion and including a wire inserted into the coil spring and fixed to a tip end portion of the coil spring, and a hardness adjuster provided at the operation portion and configured to adjust the hardness of the flexible portion in such a manner that the coil spring is compressed with a base end of the coil spring and a base end of the wire being apart from each other. The hardness adjuster includes a wire holder configured to hold a base end portion of the wire unit protruding toward the base end side beyond a base end portion of the coil spring unit, a coil spring contact portion contacting the base end portion of the coil spring unit, a relative distance changer configured to change the distance in the longitudinal direction of the operation portion between the coil spring contact portion and the wire holder, a first retainer configured to retain a retained portion at a first radial position apart from the center axis of the operation portion along the longitudinal direction by a first radius distance, the retained portion being positioned on a tip end side with respect to the base end portion of the coil spring unit, a second retainer configured to retain the base end portion of the wire unit at a second radial position apart from the center axis in a radial direction A by a second radius distance longer than the first radius distance, the base end portion of the wire unit being held by the wire holder, and a third retainer configured to retain the base end portion of the coil spring unit at a third radial position apart from the center axis in a radial direction B having a component of the radial direction A by a third radius distance longer than the first radius distance and shorter than the second radius distance, the base end portion of the coil spring unit contacting the coil spring contact portion.

According to the present invention, the retained portion on the tip end side with respect to the base end portion of the coil spring unit is, in the operation portion, retained at the first radial position by the first retainer, and the base end portion of the wire unit is retained at the second radial position by the second retainer. Thus, an arrangement space of built-in components in the operation portion can be ensured. Moreover, since the base end portion of the coil spring unit is retained at the third radial position by the third retainer, burden on the coil spring and the wire can be reduced.

According to an aspect of the present invention, the radial direction A and the radial direction B are preferably identical to each other.

According to an aspect of the present invention, the coil spring and the wire can be arranged in alignment with each other in the radial direction of the operation portion, and therefore, the burden on the coil spring and the wire can be further reduced.

According to an aspect of the present invention, the wire holder is preferably fixed relative to the operation portion, and the coil spring contact portion is preferably movable relative to the operation portion in the longitudinal direction.

According to an aspect of the present invention, the hardness of the flexible portion can be adjusted by a coil compression method by which the base end portion of the coil spring unit is pushed toward the tip end side relative to the base end portion of the wire unit.

According to an aspect of the endoscope of the present invention, the following expression is preferably satisfied:

$$(L3/L1) \times R1 \le R2 \le (L2/L1) \times R1 \quad (1)$$

where the distance in the longitudinal direction from the retained portion to the base end portion of the wire unit is L1, the distance in the longitudinal direction from the retained portion to the base end portion of the coil spring unit when the coil spring contact portion is at a middle position of a movable area in the longitudinal direction is L2, the distance in the longitudinal direction from the retained portion to the base end portion of the coil spring unit when the coil spring contact portion is at a tip end position of the movable area in the longitudinal direction is L3, the distance in the radial direction about the central axis from the retained portion to the base end portion of the wire unit is R1, and the distance in the radial direction about the central axis from the retained portion to the base end portion of the coil spring unit is R2.

According to an aspect of the present invention, since Expression (1) is satisfied, the angle of bending of the wire and the coil spring can be decreased in hardness adjustment for increasing the hardness of the flexible portion, and as a result, the burden on the wire and the coil spring can be further reduced.

According to an aspect of the present invention, the coil spring contact portion is preferably fixed relative to the operation portion, and the wire holder is preferably movable relative to the operation portion in the longitudinal direction.

According to an aspect of the present invention, the hardness of the flexible portion can be adjusted by a wire traction method by which the base end portion of the wire unit is pulled relative to the base end portion of the coil spring unit to compress the coil spring with the base end of the wire and the base end of the coil spring being apart from each other.

According to an aspect of the present invention, the following expression is satisfied:

$$(L2/L3) \times R2 \le R1 \le (L1/L3) \times R2 \quad (2)$$

where the distance in the longitudinal direction from the retained portion to the base end portion of the wire unit is L1, the distance in the longitudinal direction from the retained portion to the base end portion of the coil spring unit when the coil spring contact portion is at a middle position of a movable area in the longitudinal direction is L2, the distance in the longitudinal direction from the retained portion to the base end portion of the coil spring unit is L3, the distance in the radial direction about the central axis from the retained portion to the base end portion of the wire unit is R1, and the distance in the radial direction about the central axis from the retained portion to the base end portion of the coil spring unit is R2.

According to an aspect of the present invention, since Expression (2) is satisfied, the angle of bending of the wire and the coil spring can be decreased in hardness adjustment for increasing the hardness of the flexible portion, and as a result, the burden on the wire and the coil spring can be further reduced.

According to an aspect of the present invention, the wire unit preferably includes a wire sleeve attached to a base end portion of the wire, and the base end portion of the wire unit is preferably configured to include the wire sleeve. Of the base end portion of the wire unit, the position (the wire position) of the wire at a tip end of the wire sleeve is, in this aspect, more preferably retained at the second radial position by the second retainer. In the case of the coil compression method, the wire position is preferably a position specifying the base end portion of the wire unit to define L1 and R1 of Expression (1). Moreover, in the case of the wire traction method, the wire position is preferably a position specifying the base end portion of the wire unit to define L1, L2, and R1 of Expression (2).

According to an aspect of the present invention, the coil spring unit preferably includes a coil spring sleeve attached to a base end portion of the coil spring, and the base end portion of the coil spring unit is preferably configured to include the coil spring sleeve. Of the base end portion of the coil spring unit, the position (the sleeve position) at a base end of the coil spring sleeve is, in this aspect, more preferably retained at the third radial position by the third retainer. In the case of the coil compression method, the sleeve position is preferably a position specifying the base end portion of the coil spring unit to define L2, L3, and R2 of Expression (1). Moreover, in the case of the wire traction method, the sleeve position is preferably a position specifying the base end portion of the coil spring to define L3 and R2 of Expression (2).

In order to accomplish the above-described goal, the hardness adjustment device of the present invention is a hardness adjustment device provided at an endoscope including an insertion portion having a flexible portion and an operation portion provided continuously to a base end side of the insertion portion. The hardness adjustment device includes a coil spring unit including a coil spring provided to extend from the flexible portion to the operation portion, a wire unit provided to extend from the flexible portion to the operation portion and including a wire inserted into the coil spring and fixed to a tip end portion of the coil spring, and a hardness adjuster provided at the operation portion and configured to adjust the hardness of the flexible portion in such a manner that the coil spring is compressed with a base end of the coil spring and a base end of the wire being apart from each other. The hardness adjuster includes a wire holder configured to hold a base end portion of the wire unit protruding toward the base end side beyond a base end portion of the coil spring unit, a coil spring contact portion contacting the base end portion of the coil spring unit, a relative distance changer configured to change the distance in the longitudinal direction of the operation portion between the coil spring contact portion and the wire holder, a first retainer configured to retain a retained portion at a first radial position apart from the center axis of the operation portion along the longitudinal direction by a first radius distance, the retained portion being positioned on a tip end side with respect to the base end portion of the coil spring unit, a second retainer configured to retain the base end portion of the wire unit at a second radial position apart from the center axis in a radial direction A by a second radius distance longer than the first radius distance, the base end portion of the wire unit being held by the wire holder, and a third retainer configured to retain the base end portion of the coil spring unit at a third radial position apart from the center axis in a radial direction B having a component of the radial direction A by a third radius distance longer than the first radius distance and shorter than the second radius distance, the base end portion of the coil spring unit contacting the coil spring contact portion.

According to the present invention, the retained portion on the tip side with respect to the base end portion of the coil spring unit is, in the operation portion, retained at the first radial position by the first retainer, and the base end portion of the wire unit is retained at the second radial position by the second retainer. Thus, the arrangement space of the built-in components in the operation portion can be ensured. Moreover, since the base end portion of the coil spring unit is retained at the third radial position by the third retainer, the burden on the coil spring and the wire can be reduced.

According to the present invention, the arrangement space of the built-in components in the operation portion can be ensured, and the burden on the coil spring and the wire can be reduced.

BRIEF DESCRIPTION OF THE DRAWINGS

FIG. 8 is a view for describing features in hardness adjustment of the hardness adjuster of the present invention;

FIGS. 10A to 10D are views for describing features of a distance adjustment mechanism;

DETAILED DESCRIPTION OF THE PREFERRED EMBODIMENTS

An endoscope and a hardness adjustment device according to the present invention will be described below with reference to attached drawings.

Figure 1:
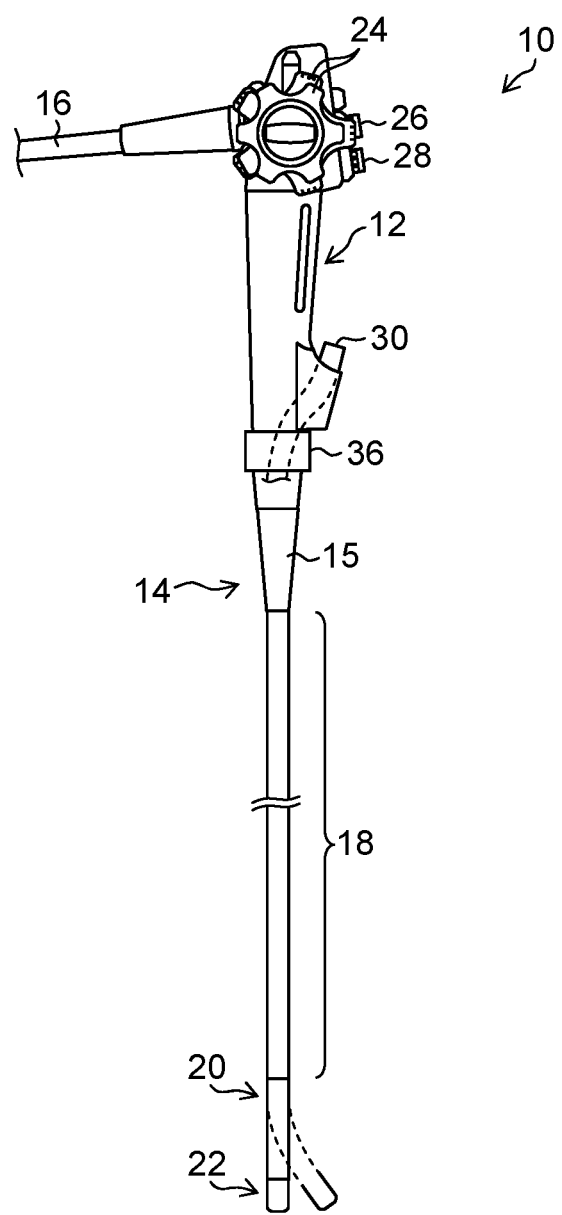
FIG. 1 is a view of an entire configuration of an endoscope.

FIG. 1 is a view of an entire configuration of an endoscope 10 of an embodiment of the present invention.

[Configuration of Endoscope 10]

The endoscope 10 of the present embodiment includes an operation portion 12 and an insertion portion 14 provided continuously to the operation portion 12.

A base end of a universal cable 16 is connected to a base end side of the operation portion 12, and a tip end of the universal cable 16 is provided with a light source connector (not shown). The light source connector is connected to a light source device (not shown) such that illumination light is sent to an illumination optical system disposed on a tip end surface of the insertion portion 14. Moreover, an electric connector (not shown) is also connected to the light source connector. By connection of the electric connector to an endoscope processor (not shown), data of an observation image acquired by an observation optical system disposed on the tip end surface of the insertion portion 14 is output to the endoscope processor, and then, an image of an observation site is displayed on a monitor device (not shown) connected to the endoscope processor.

A base end side of the insertion portion 14 is provided continuously to a tip end side of the operation portion 12 through an anti-bending cover member 15. In the present embodiment, the operation portion 12 including the cover member 15 is referred to as an "operation portion 12."

The insertion portion 14 includes, in the order from a base end portion to a tip end portion of the insertion portion 14, a flexible portion 18, a curvable portion 20, and a tip end hard portion 22. The curvable portion 20 is curvably and remotely operated by rotation of angle knobs 24 provided on the base end side of the operation portion 12. This allows a tip end surface of the tip end hard portion 22 to face in a desired direction.

The operation portion 12 is further provided with an air/water supply button 26 for air/water supply from an air/water supply port (not shown) of the tip end hard portion 22 to an examination site etc. through an air/water supply channel (not shown) inserted into the insertion portion 14, a suction button 28 for suction from a forceps port (not shown) of the tip end hard portion 22 through a forceps channel (not shown) inserted into the insertion portion 14, and a forceps insertion port 30 as an opening communicating with the forceps channel (not shown) and formed for insertion of forceps by a practitioner, for example.

Further, the endoscope 10 is equipped with the hardness adjustment device of the present embodiment. The hardness adjustment device includes a hardness adjustment unit 32 (see FIG. 2) configured to substantially adjust the hardness of the flexible portion 18, and a hardness adjuster 34 (see FIGS. 3 to 8) configured to operate the hardness adjustment unit 32. Reference numeral 36 in FIG. 1 designates an operation ring configured to operate the hardness adjuster 34, and the operation ring 36 is rotatably operated by the practitioner operating the endoscope 10.

<Hardness Adjustment Unit 32, Hardness Adjuster 34>

Figure 2:
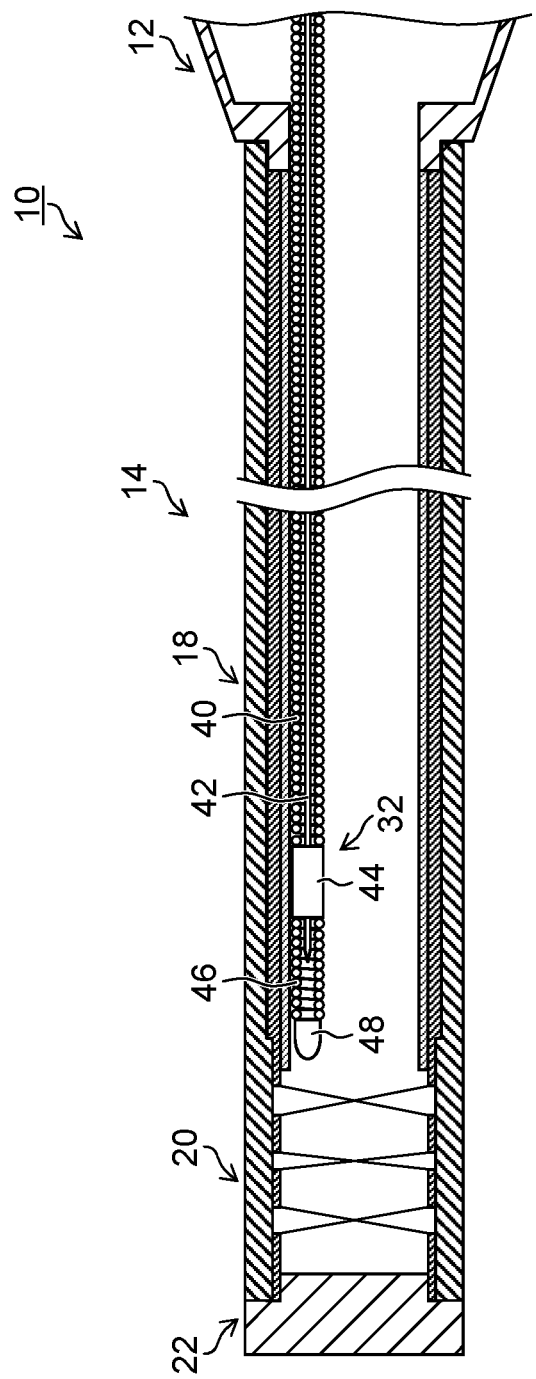
FIG. 2 is a longitudinal sectional view of an insertion portion of the endoscope illustrating a hardness adjustment unit configuration.

FIG. 2 is a longitudinal sectional view of the insertion portion 14. In FIG. 2, the flexible portion 18 is illustrated as if the flexible portion 18 is cut off, and for the sake of avoiding complexity of the drawing, the hardness adjustment unit 32 including a coil spring 40 and a wire 42 is mainly illustrated. Note that in each of the operation portion 12 and the insertion portion 14 as illustrated in FIG. 1, a plurality of well-known built-in components such as a treatment tool insertion channel, a curving operation wire, an air/water supply conduit, a light guide, and a signal line are arranged in addition to the hardness adjustment unit 32. These built-in components are, without any clearances thereamong, loaded in the insertion portion 14 so that the diameter of the insertion portion 14 can be reduced.

Figure 3:
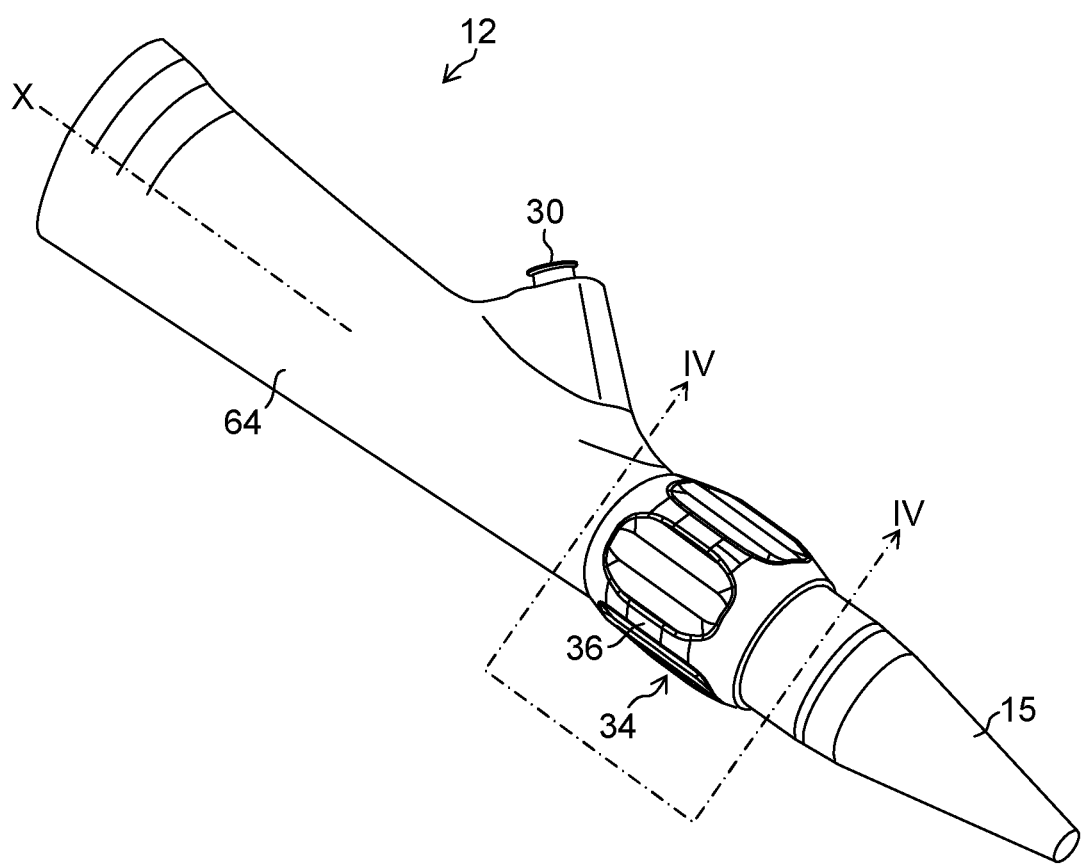
FIG. 3 is a view of an outer appearance of an operation ring provided at the operation portion.
Figure 4:
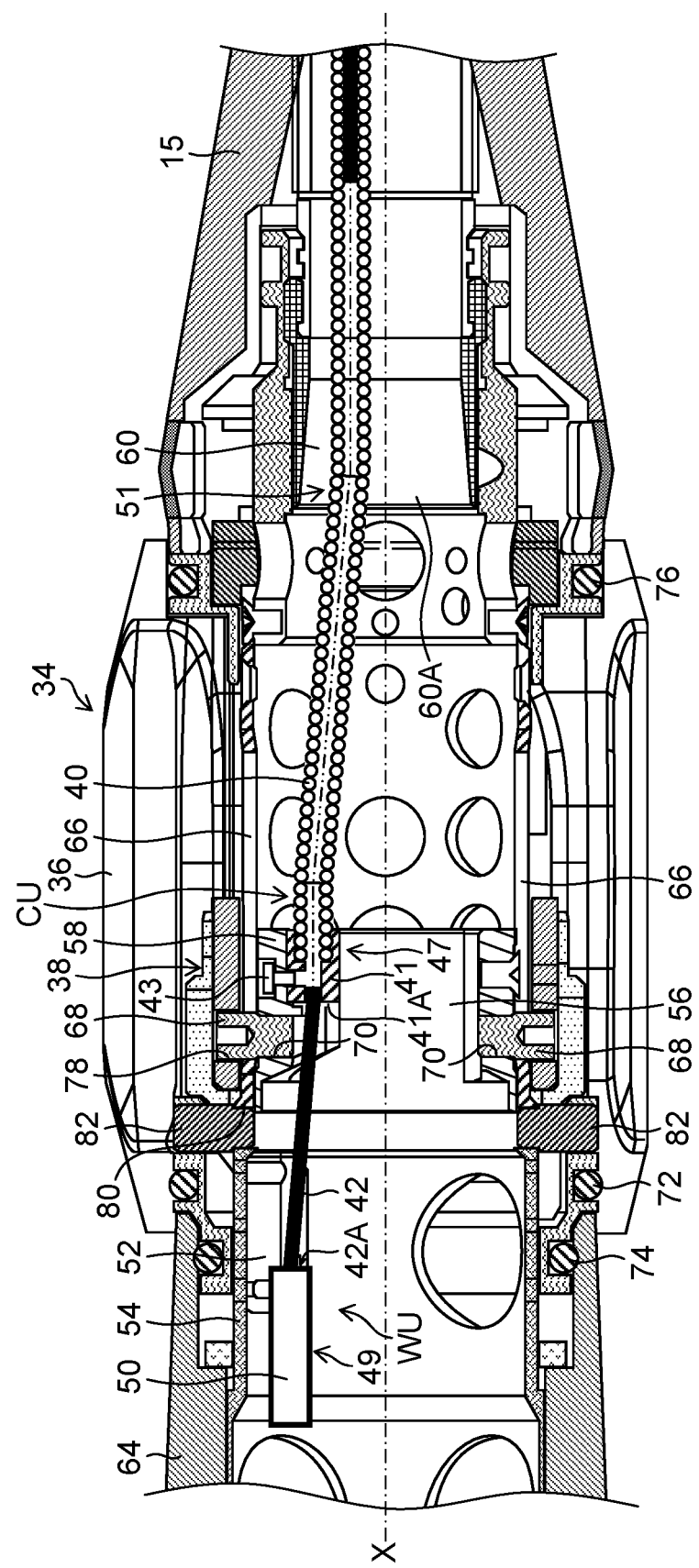
FIG. 4 is a partial cross-sectional view for describing a hardness adjuster.
Figure 5A:
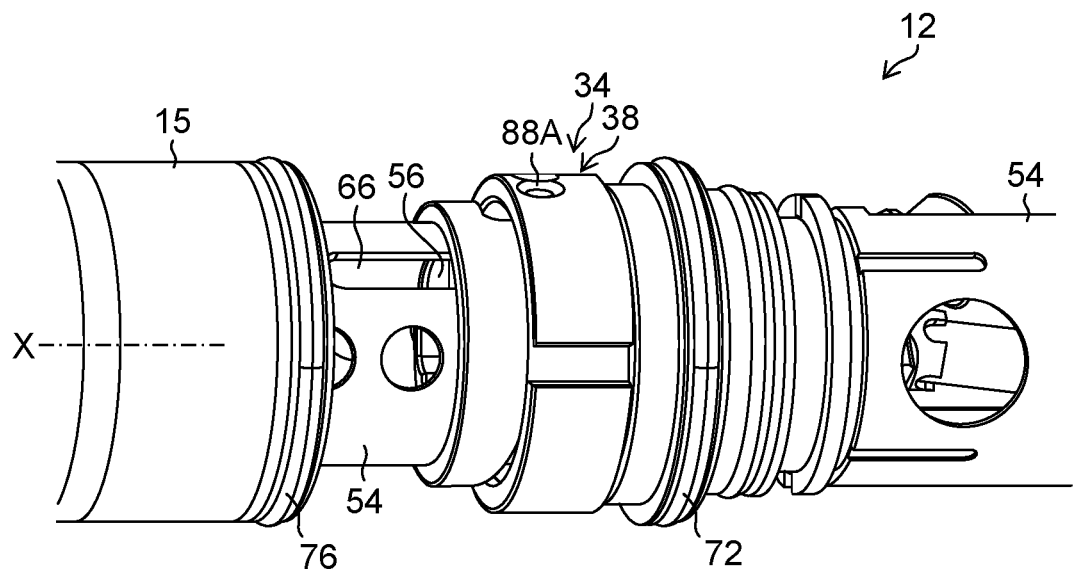
FIGS. 5A and 5B are views of an outer appearance of the operation portion from which an operation ring and a cam ring are detached.
Figure 5B:
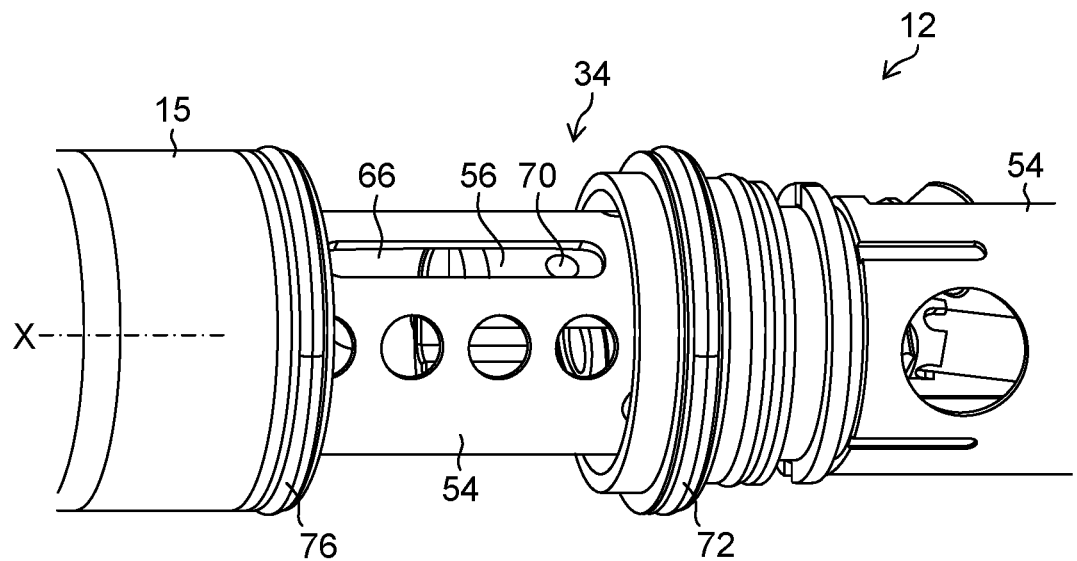

FIG. 3 is a perspective view of an outer appearance of the operation portion 12 including the operation ring 36 provided on the tip end side of the operation portion 12. Moreover, FIG. 4 is a cross-sectional view along an IV-IV line of FIG. 3 for the purpose of describing an internal structure of the hardness adjuster 34. Further, FIG. 5A is a perspective view of an outer appearance of a main portion of the operation portion 12 of FIG. 3, the operation ring 36 being detached from the operation portion 12. FIG. 5B is a perspective view of an outer appearance of a main portion of the operation portion 12 of FIG. 5A, a cam ring 38 being further removed from the operation portion 12. The cam ring 38 will be described later.

In the present embodiment, the hardness adjustment unit 32 mainly includes a wire unit WU and a coil spring unit CU as illustrated in FIG. 4. The wire unit WU includes a wire sleeve 50 attached to a base end portion of the wire 42, and a base end portion 49 of the wire unit WU is configured to include the wire sleeve 50. The coil spring unit CU includes a coil spring sleeve 41 attached to a base end portion of the coil spring 40, and a base end portion 47 of the coil spring unit CU is configured to include the coil spring sleeve 41.

The types of hardness adjuster 34 configured to change a compression state of the coil spring 40 of the hardness adjustment unit 32 employ a wire traction method and a coil compression method.

According to the wire traction method, the base end portion 49 of the wire unit WU is pulled relative to the base end portion 47 of the coil spring unit CU. According to the coil compression method, the base end portion 47 of the coil spring unit CU is, toward the tip end side, pushed relative to the base end portion 49 of the wire unit WU. Even in the wire traction type or the coil compression type hardness adjuster 34, the hardness of the flexible portion 18 can be adjusted in such a manner that the coil spring 40 is compressed with a base end of the coil spring 40 and a base end of the wire 42 being apart from each other.

In the present embodiment, the case of employing the coil compression method will be described. However, the present invention is also similarly applicable to the wire traction method.

Note that a "longitudinal direction" as described later indicates the axial direction of the operation portion 12 formed in a tubular shape, and an "X-axis" illustrated in FIGS. 3, 4, etc. indicates the central axis X of the operation portion 12 along the "longitudinal direction" of the operation portion 12.

Returning to FIG. 2, the coil spring 40 is provided to extend from the flexible portion 18 to the operation portion 12. Moreover, the wire 42 is provided to extend from the flexible portion 18 to the operation portion 12, and is inserted into a hollow portion of the coil spring 40. A tip end portion of each of the wire 42 and the coil spring 40 is fixed to a base end portion of a relay metal fitting 44 by a fixing method such as brazing. That is, a fixing portion to be fixed to the tip end portion of the coil spring 40 is provided at the tip end portion of the wire 42.

A base end portion of a short coil spring 46 as a cushion member is connected to a tip end portion of the relay metal fitting 44, and a metal fitting 48 is fixed to a tip end portion of the coil spring 46. The relay metal fitting 44, the coil spring 46, and the metal fitting 48 are not fixed to the insertion portion 14, and therefore, a tip end portion of the hardness adjustment unit 32 is formed as a free end.

As illustrated in FIG. 4, the base end portion 49 of the wire unit WU protrudes toward the base end side beyond the base end portion 47 of the coil spring unit CU. Moreover, the wire sleeve 50 forming the base end portion 49 of the wire unit WU is fixed to an inner peripheral surface of a tubular fixing frame 54 through a wire holder 52 as a second retainer provided at the operation portion 12. The wire sleeve 50 is a member integrally attached to the wire 42 to retain the base end portion of the wire 42 at a predetermined radial position (a second radial position), and forms some of components of the wire unit WU. That is, the base end portion 49 of the wire unit WU in the present embodiment includes not only the base end portion of the wire 42, but also the wire sleeve 50 integrally attached to the base end portion of the wire 42.

Moreover, the base end portion 47 of the coil spring unit CU is supported in contact with a coil spring contact portion 58 as a third retainer provided at a later-described movable ring 56. The coil spring contact portion 58 applies compression force in a coil spring axial direction to the coil spring 40 by forward movement of the movable ring 56 toward the tip end side.

FIG. 4 illustrates the cross-sectional view of the base end portion 47 of the coil spring unit CU. The base end portion 47 of the coil spring unit CU is configured to include the coil spring sleeve 41. A base end side of the coil spring 40 is inserted into the coil spring sleeve 41, and is fixed to the coil spring sleeve 41 by brazing. Moreover, the coil spring sleeve 41 is fixed to the coil spring contact portion 58 with a screw 43 screwed from the outer periphery of the movable ring 56, and therefore, is supported in contact with the coil spring contact portion 58. The coil spring sleeve 41 is a member integrally attached to the coil spring 40 to retain the base end portion of the coil spring 40 at a predetermined radial position (a third radial position), and forms some of components of the coil spring unit CU. That is, the base end portion 47 of the coil spring unit CU in the present embodiment includes not only the base end portion of the coil spring 40, but also the coil spring sleeve 41 integrally attached to the base end portion of the coil spring 40.

The coil spring unit CU includes a retained portion 51, and the retained portion 51 is positioned on the tip end side with respect to the base end portion 47 of the coil spring unit CU. The operation portion 12 is provided with a tubular coil spring holder 60 as a first retainer configured to hold the retained portion 51. The retained portion 51 is, by the built-in components, pressed in contact with a tapered surface 60A formed on a base end side of the coil spring holder 60, and therefore, is held by the coil spring holder 60. The tapered surface 60A is formed such that the diameter of the coil spring holder 60 increases toward the base end side.

Although operation of the hardness adjustment device will be described later, the operation ring 36 of the hardness adjuster 34 is rotatably operated, and then, the movable ring 56 moves forward to the tip end side to compress the coil spring 40 in the axial direction. Moreover, the movable ring 56 moves backward to the base end side to return the coil spring 40 from a compressed state to a natural length.

The hardness adjuster 34 includes the cylindrical operation ring 36, the cam ring 38, and the movable ring 56. The operation ring 36, the cam ring 38, and the movable ring 56 forms an example of a relative distance changer configured to change the distance in the longitudinal direction of the operation portion 12 between the coil spring contact portion 58 and the wire holder 52.

As illustrated in FIG. 4, a main body 64 and the cover member 15 in the operation portion 12 are coupled together through the fixing frame 54.

As illustrated in FIGS. 5A and 5B, the fixing frame 54 is provided with elongated hole-shaped linear grooves 66 along the longitudinal direction. The linear grooves 66 are provided respectively at two positions at equal interval in the circumferential direction of the fixing frame 54.

The cylindrical movable ring 56 is slidably disposed on the inner peripheral surface of the fixing frame 54. The phase of being "slidably disposed" means that an outer peripheral surface of the movable ring 56 and the inner peripheral surface of the fixing frame 54 are arranged in contact with each other to such an extent that the movable ring 56 can smoothly slide in the longitudinal direction.

A first cam pin 68 of a cam mechanism engages with each linear groove 66 of the fixing frame 54, as illustrated in FIG. 4. The movable ring 56 is provided with pin holes 70 into each of which a base end portion of a corresponding one of the first cam pins 68 is inserted and fixed. Thus, the movable ring 56 is guided by the linear grooves 66 and the first cam pins 68 to move back and forth in the longitudinal direction of the fixing frame 54.

The cam ring 38 is disposed on an outer peripheral surface of the fixing frame 54 between the main body 64 and the cover member 15. Moreover, the operation ring 36 is disposed on an outer peripheral surface of the cam ring 38, and the cam ring 38 rotates about the central axis X in accordance with rotary operation of the operation ring 36. As illustrated in FIGS. 4 and 5, water-tightness between the operation ring 36 and the main body 64 is ensured by a pair of packing rings 72, 74, and water-tightness between the operation ring 36 and the cover member 15 is ensured by a packing ring 76.

Figure 6A:
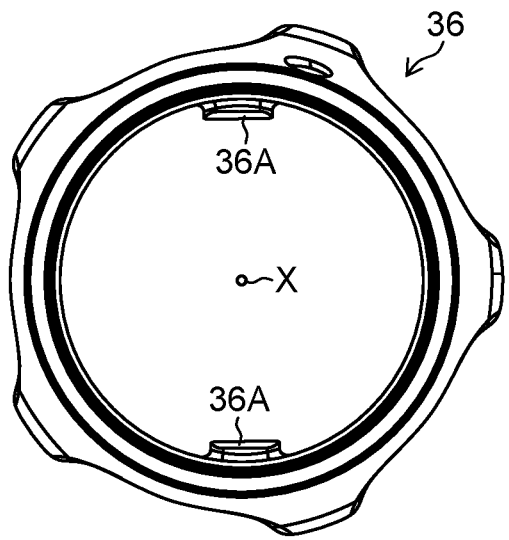
FIG. 6A is a front view of the operation ring.
Figure 6B:
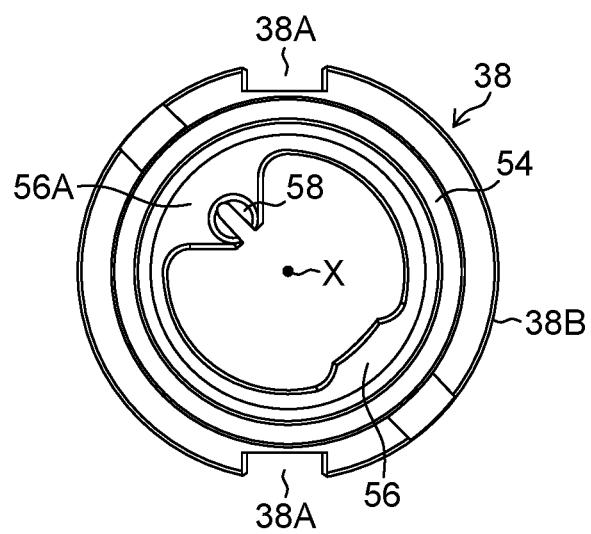
FIG. 6B is a front view of the cam ring etc.

FIG. 6A is a front view of the operation ring 36, and FIG. 6B is a front view of the cam ring 38, the fixing frame 54, and the movable ring 56. According to FIGS. 6A and 6B, a pair of keys 36A protruding from an inner peripheral surface of the operation ring 36 engages with a pair of key grooves 38A formed at the outer peripheral surface of the cam ring 38. Thus, the cam ring 38 rotates in accordance with the rotary operation of the operation ring 36.

An inner peripheral surface of the movable ring 56 is provided with the coil spring contact portion 58 contacting and supporting the coil spring sleeve 41 of the coil spring 40 of FIG. 4. The coil spring contact portion 58 is provided at a thick portion 56A of the inner peripheral surface of the movable ring 56, and therefore, strength is ensured.

<<Cam Mechanism of Cam Ring 38>>

Figure 7:
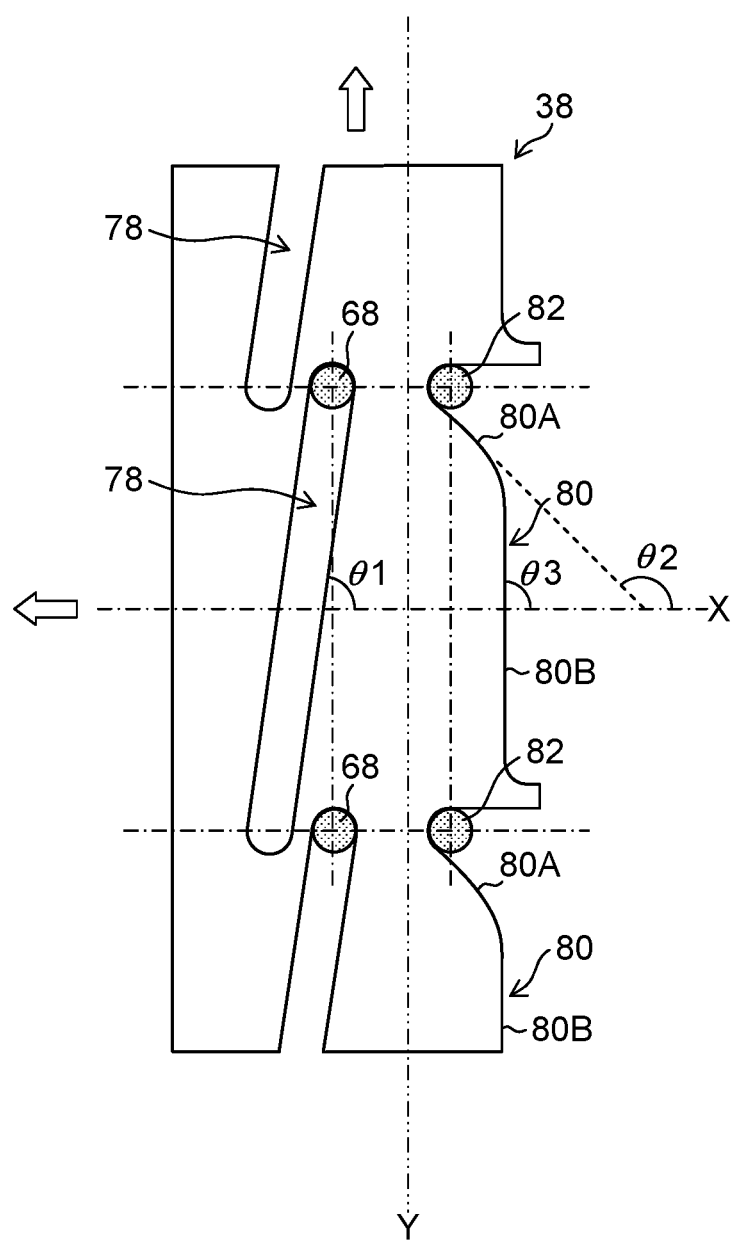
FIG. 7 is a development view of the cam ring.

FIG. 7 is a development view of the cylindrical cam ring 38. Cam grooves and cam pins engaging respectively with the cam grooves will be described with reference to FIG. 7, the cam grooves and the cam pins forming the cam mechanism of the cam ring 38.

The cam ring 38 is provided with a pair of first cam grooves 78 and a pair of second cam grooves 80 extending in the circumferential direction of the cam ring 38. The "circumferential direction" in FIG. 7 indicates a Y-direction perpendicular to the central axis X.

The first cam grooves 78 are provided on a tip end side of the cam ring 38, and the second cam grooves 80 are provided on a base end side of the cam ring 38. Moreover, each first cam groove 78 is formed in an elongated hole shape. On the other hand, each second cam groove 80 is not formed in an elongated hole shape, but is formed in such a manner that a base end edge of the cam ring 38 is cut out.

Each first cam groove 78 has an inclination angle θ1 with respect to the central axis X. The second cam grooves 80 include an inclined groove 80A having an inclination angle θ2 different from the inclination angle θ1 with respect to the central axis X, and a vertical groove 80B provided continuously to the inclined groove 80A and having the vertical angle θ3 with respect to the central axis X.

Thus, the first cam grooves 78 and the second cam grooves 80 each have a component in the Y-direction as the circumferential direction and a component in the direction along the central axis X. Note that the vertical groove 80B may incline to a certain degree. A relationship among the inclination angle θ1, the inclination angle θ2, and the vertical angle θ3 is set at θ1<θ3<θ2. Note that in the present embodiment, description will be made supposing that θ3 is 90°.

Each first cam pin 68 engages with a corresponding one of the first cam grooves 78. As illustrated in FIGS. 4 and 5, the base end portion of each first cam pin 68 is, through a corresponding one of the linear grooves 66 formed at the fixing frame 54, inserted and fixed into a corresponding one of the pin holes 70 of the movable ring 56. That is, the first cam pin 68 engages with both of the linear groove 66 of the fixing frame 54 and the first cam groove 78 of the cam ring 38. Thus, in rotation of the cam ring 38, the movable ring 56 moves, by linear action of the first cam grooves 78 and the linear grooves 66, back and forth in the longitudinal direction of the fixing frame 54 along the linear grooves 66.

On the other hand, each second cam pin 82 contacts a corresponding one of the second cam grooves 80 of FIG. 7. As illustrated in FIG. 4, a base end portion of each second cam pin 82 is fixed to the fixing frame 54. Thus, the second cam pin 82 serves as a fixed pin which does not move from a fixed position. Thus, in a rotation range of the cam ring 38 while the inclined groove 80A of the second cam grooves 80 is moving in contact with the second cam pin 82, the cam ring 38 moves forward to the tip end side along the central axis X. In an initial state, each second cam groove 80 may form a clearance without contacting a corresponding one of the second cam pins 82. Such a clearance provides an effect of absorbing relative movement between the end portion of the wire 42 and the end portion of the coil spring 40 due to curving of the flexible portion 18. That is, the clearance functions as an allowance for a hardness adjustment function. Note that in the embodiment described below, description will be made supposing that no clearance is formed.

Note that the shape of the inclined groove 80A is preferably set such that a first movement distance of the cam ring 38 moving forward along the central axis X in rotation of the cam ring 38 is longer than a second movement distance of the movable ring 56 moving forward along the central axis X by the first cam grooves 78. Moreover, in further rotation of the cam ring 38, the cam ring 38 does not move forward along the central axis X within the rotation range in which the vertical groove 80B moves in contact with a corresponding one of the second cam pins 82. Thus, in the rotation range in which the vertical groove 80B contacts a corresponding one of the second cam pins 82, the movable ring 56 only moves forward in accordance with movement of each first cam groove 78 along a corresponding one of the first cam pins 68.

[Description of Operation of Hardness Adjuster 34]

FIG. 8 is a view for describing operation of the hardness adjuster 34 configured to change the compression state of the coil spring 40. In FIG. 8, an X-axis indicates the central axis X of the operation portion 12 (see FIG. 3), and a Y-axis indicates the circumferential direction of the cam ring 38.

In the form of the hardness adjuster 34 before operation as illustrated in the portion (A) of FIG. 8, each of the first cam pins 68 and the second cam pins 82 is at a corresponding one of hardness adjustment start positions P as upper end positions of the first cam grooves 78 and the second cam grooves 80.

Next, as illustrated in the portion (B) of FIG. 8, when the operation ring 36 rotates such that the cam ring 38 rotates in the direction indicated by an arrow of the circumferential direction (i.e., a Y-axis direction), the inclined groove 80A having the inclination angle θ2 moves in contact with a corresponding one of the second cam pins 82 as the fixed pins. Accordingly, the cam ring 38 moves, by ΔL1 forward to the tip end side along the central axis X.

Further, each first cam pin 68 moves along a corresponding one of the first cam grooves 78 by rotation of the cam ring 38, and therefore, the movable ring 56 moves, by ΔL2, forward to the tip end side of the fixing frame 54.

That is, the cam ring 38 rotates such that each of the first cam pins 68 and the second cam pins 82 moves from the P position of the portion (A) of FIG. 8 to a Q position of the portion (B) of FIG. 8, and therefore, the movable ring 56 greatly moves forward by a distance of ΔL1+ΔL2.

By forward movement of the movable ring 56, the coil spring contact portion 58 of the movable ring 56 pushes the base end portion 47 of the coil spring unit CU toward the tip end side in the longitudinal direction of the operation portion 12. This compresses the coil spring 40, thereby increasing the hardness of the flexible portion 18.

At an initial phase of operation of the hardness adjuster 34, the coil spring 40 is in a natural length state, and no great force is required in compression of the coil spring 40.

Thus, in the hardness adjuster 34, the inclination angle θ2 of the inclined groove 80A of the second cam grooves 80 of the cam ring 38 is equal to or higher than 90 degrees, and therefore, the cam ring 38 can greatly move forward along the central axis X only by a small amount of rotation of the cam ring 38 from FIG. 8. That is, a great amount of compression of the coil spring 40 can be ensured only by a small amount of rotation at the initial phase of operation of the cam ring 38, leading to efficient hardness adjustment operation.

The operation ring 36 further rotates the cam ring 38 in the same direction such that each of the first cam pins 68 and the second cam pins 82 moves from the Q position of the portion (B) of FIG. 8 to a hardness adjustment end position M of the portion (E) of FIG. 8 by way of the portions (C) and (D) of FIG. 8. This compresses the coil spring 40 to the maximum extent, and therefore, the hardness of the flexible portion 18 is highest.

Operation from the P position of the portion (A) of FIG. 8 to the Q position of the portion (B) of FIG. 8 is the initial phase of operation, whereas operation from the Q position of the portion (B) of FIG. 8 to the M position of the portion (E) of FIG. 8 is a stationary phase of operation.

In rotation of the cam ring 38 at the stationary phase of operation, the vertical groove 80B having the vertical angle θ3 contacts a corresponding one of the second cam pins 82, and therefore, the cam ring 38 does not move forward. Meanwhile, each first cam groove 78 engages with a corresponding one of the first cam pins 68, and therefore, the movable ring 56 moves, according to the amount of rotation of the cam ring 38, forward to the tip end side by the inclination angle θ1 of the first cam groove 78.

By forward movement of the movable ring 56, the movable ring 56 further pushes the coil spring 40 toward the tip end side of the fixing frame 54 in the longitudinal direction. This firmly compresses the coil spring 40, and therefore, the hardness of the flexible portion 18 gradually increases.

After repeated use of the hardness adjustment unit 32, the coil spring 40 is plastically deformed (so-called "spring settling"), and the length of the coil spring 40 is shortened due to settling of the coil spring 40. Thus, the cam ring 38 moves toward the tip end side through the movable ring 56, and therefore, each second cam groove 80 is separated from a corresponding one of the second cam pins 82 toward the tip end side. As a result, even when the base end portion 47 of the coil spring unit CU is pushed by the coil spring contact portion 58, the amount of pushing decreases by separation of the second cam groove 80 from the second cam pin 82 toward the tip end side, leading to lower operability of the hardness adjuster 34.

For this reason, a distance adjustment mechanism 62 for spring settling adjustment is provided at the cam ring 38.

<Distance Adjustment Mechanism 62>

Figure 9A:
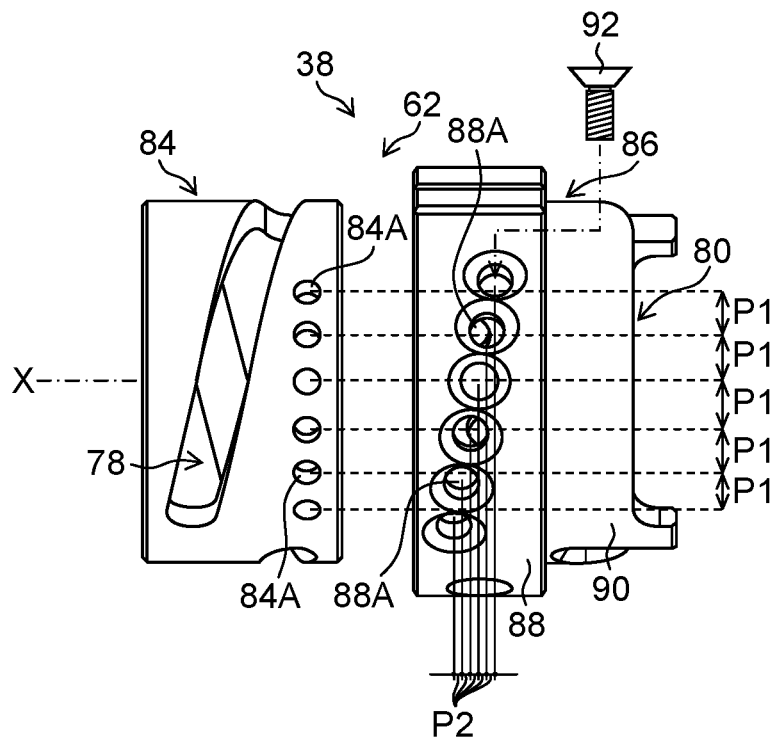
FIGS. 9A and 9B are views of a distance adjustment mechanism configuration in the hardness adjuster.
Figure 9B:
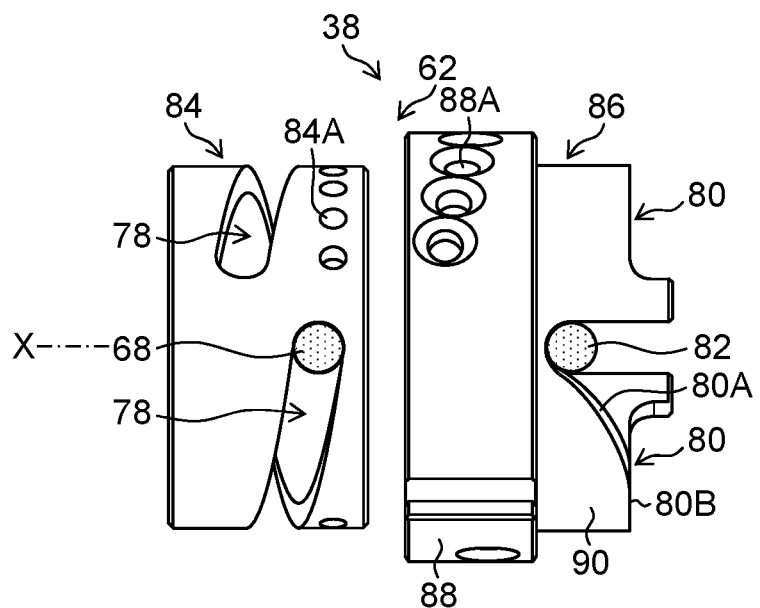

FIGS. 9A and 9B are side views of the distance adjustment mechanism 62 from different angles in the circumferential direction of the cam ring 38.

The cam ring 38 is, in the longitudinal direction, divided into a first ring 84 with the first cam grooves 78 and a second ring 86 with the second cam grooves 80.

According to the distance adjustment mechanism 62, a coupling position between the first ring 84 and the second ring 86 changes from a first axial position in the longitudinal direction to a second axial position different from the first axial position such that the distance in the longitudinal direction between an engagement position at which each first cam pin 68 engages with a corresponding one of the first cam grooves 78 and a contact position at which each second cam pin 82 contacts a corresponding one of the second cam grooves 80 is adjusted.

A plurality of screw holes 84A (six screw holes 84A) are formed in the circumferential direction on the base end side of the first ring 84. A plurality of coupling holes 88A (six coupling holes 88A) are formed in a diagonal circumferential direction at a tip end side large-diameter portion 88 of the second ring 86. The large-diameter portion 88 is fitted onto the outer periphery of the base end side of the first ring 84, and when the first ring 84 and the second ring 86 are coupled together, also functions as a stopper member configured to cover the outer periphery of the first cam pins 68 to prevent each first cam pin 68 from dropping from a corresponding one of the pin holes 70. Moreover, the second ring 86 also has, on the base end side, a small-diameter portion 90 having the same diameter as that of the first ring 84.

The six screw holes 84A in the circumferential direction of the first ring 84 and the six coupling holes 88A in the diagonal circumferential direction of the second ring 86 are, as indicated by dashed lines of FIG. 9A, formed at equal pitch P1 in the circumferential direction. Moreover, for the six coupling holes 88A in the diagonal circumferential direction of the second ring 86, a pitch P2 in the longitudinal direction is preferably about 0.3 to 0.7 mm.

Thus, while the large-diameter portion 88 of the second ring 86 is being fitted onto the first ring 84, the lowermost screw hole 84A and the lowermost coupling hole 88A first overlap with each other in FIG. 9A, and then, the second screw hole 84A from the bottom and the second coupling hole 88A from the bottom overlap with each other. Eventually, the uppermost screw hole 84A and the uppermost coupling hole 88A overlap with each other.

Then, each pair of the screw hole 84A and the coupling hole 88A overlapping with each other is fastened with a countersunk screw 92, and therefore, the first ring 84 and the second ring 86 are integrally coupled together. Note that in the case where the screw holes 84A are mere through-holes, pins can be used instead of the countersunk screws 92.

<Spring Settling Adjustment Method>

FIGS. 10A to 10D are views for describing the method for adjusting settling of the coil spring 40 by the distance adjustment mechanism 62.

In description made below, the phrasing of "the uppermost screw hole/coupling hole" and "the lowermost screw hole/coupling hole" will be used for the six screw holes 84A formed at the first ring 84 and the six coupling holes 88A formed at the second ring 86, and means the uppermost screw hole/coupling hole and the lowermost screw hole/coupling hole as viewed in FIG. 9A.

As illustrated in FIG. 10A, the uppermost screw hole 84A of the first ring 84 and the uppermost coupling hole 88A of the second ring 86 are fastened together with the countersunk screw 92 (see FIG. 9A) in the state in which the uppermost screw hole 84A and the uppermost coupling hole 88A overlap with each other. This forms the cam ring 38 of FIG. 10B. The cam ring 38 of FIG. 10B is in a spring settling pre-adjustment form in which no settling is caused at the coil spring 40.

At this point, the distance in the longitudinal direction between the first cam pin 68 engaging with the first cam groove 78 and the second cam pin 82 contacting the second cam groove 80 is indicated by "W1." The distance W1 is the distance from the center position of the cam pin. Moreover, the position of the first cam pin 68 with respect to the first cam groove 78 and the position of the second cam pin 82 with respect to the second cam groove 80 in FIG. 10B are the hardness adjustment start positions P of the portion (A) of FIG. 8.

Thereafter, when settling is caused at the coil spring 40 due to repeated use of the hardness adjustment unit 32, the countersunk screws 92 are first detached from the cam ring 38 of FIG. 10B. Then, as illustrated in FIG. 10C, the first ring 84 is pulled in the direction of an arrow along the longitudinal direction, and accordingly, is detached from the second ring 86 into which the first ring 84 is fitted. In this case, each second cam pin 82 is unmovably fixed to the fixing frame 54, but each first cam pin 68 is fixed to the movable ring 56 movable on the fixing frame 54 in the longitudinal direction. Thus, the first cam pins 68 are movable. Consequently, the first ring 84 can be detached from the second ring 86 without detaching each first cam pin 68 from a corresponding one of the first cam grooves 78.

Next, the first ring 84 is, as illustrated in FIG. 10C, fitted into the second ring 86 with the lowermost screw hole 84A of the first ring 84 and the lowermost coupling hole 88A of the second ring 86 overlapping with each other, and the first ring 84 and the second ring 86 are fastened together with the countersunk screws 92 as illustrated in FIG. 10D. At this point, W2 is longer than W1, where the distance in the longitudinal direction between the first cam pin 68 engaging with the first cam groove 78 and the second cam pin 82 contacting the second cam groove 80 is indicated by "W2."

That is, when the first ring 84 is fitted into the second ring 86 with the lowermost screw hole 84A of the first ring 84 and the lowermost coupling hole 88A of the second ring 86 overlapping with each other, a fitting width is smaller than the case where the first ring 84 is fitted into the second ring 86 with the uppermost screw hole 84A of the first ring 84 and the uppermost coupling hole 88A of the second ring 86 overlapping with each other. The "fitting width" means an overlapping width between the first ring 84 and the large-diameter portion 88 of the second ring 86 when the first ring 84 is fitted into the large-diameter portion 88.

Thus, the distance in the longitudinal direction between the first cam groove 78 and the second cam groove 80 in the case of FIG. 10D is longer than that in the case of FIG. 10B. Moreover, each second cam pin 82 is fixed, and is at the same position as that in the case of FIG. 10B. Thus, the first cam pins 68 move toward the tip end side in the longitudinal direction by W2−W1=ΔW. That is, the position of the movable ring 56 moves forward to the tip end side in the longitudinal direction by ΔW.

With this configuration, even when the coil spring 40 is shortened due to spring settling, the movable ring 56 moves forward to the tip end side in the longitudinal direction, and therefore, spring settling can be adjusted.

<Endoscope 10 and Hardness Adjustment Device>

The hardness adjuster 34 of the endoscope 10 of the present embodiment includes, as illustrated in FIG. 4, the coil spring holder 60 configured to hold the retained portion 51 on the tip end side with respect to the base end portion 47 of the coil spring unit CU, the wire holder 52 configured to hold the base end portion 49 of the wire unit WU protruding toward the base end side beyond the base end portion 47 of the coil spring unit CU, and the coil spring contact portion 58 configured to contact the base end portion 47 of the coil spring unit CU to apply compression force in the coil spring axial direction to the coil spring 40.

As described above, the hardness adjuster 34 includes, as the example of the relative distance changer, the operation ring 36, the cam ring 38, and the movable ring 56.

Figure 11:
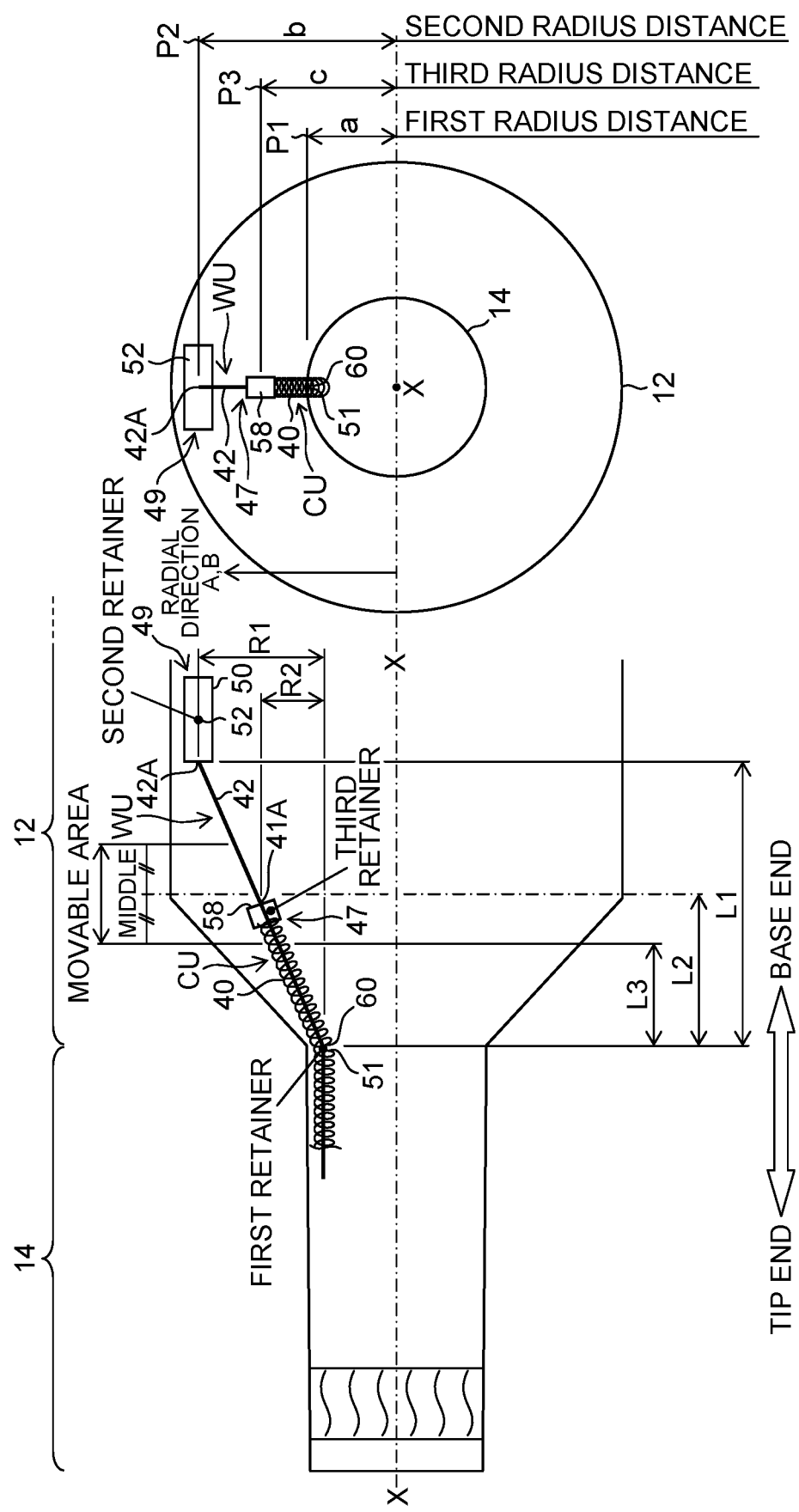
FIG. 11 is a view for describing a coil compression method, and illustrates the arrangement positions of a coil spring holder, a wire holder, and a coil spring contact portion in the longitudinal direction of the operation portion.

FIG. 11 is a view for describing the coil compression method, and illustrates the arrangement positions of the coil spring holder 60, the wire holder 52, and the coil spring contact portion 58 in the longitudinal direction of the operation portion 12.

The coil spring holder 60 functions as the first retainer configured to retain the retained portion 51 of the coil spring unit CU at a first radial position P1 apart from the central axis X of the operation portion 12 by a first radius distance a.

The wire holder 52 functions as the second retainer configured to retain the base end portion 49 of the wire unit WU at a second radial position P2 apart from the central axis X in a radial direction A by a second radium distance b longer than the first radius distance a. Note that in the present embodiment, the following form is preferably employed. Of the base end portion 49 of the wire unit WU, the position (the wire position) 42A of the wire at a tip end of the wire sleeve 50 is retained at the second radial position P2 by the wire holder 52.

The coil spring contact portion 58 functions as the third retainer configured to retain the base end portion 47 of the coil spring unit CU at a third radial position P3 apart from the central axis X in a radial direction B having a component of the radial direction A by a third radius distance c longer than the first radius distance a and shorter than the second radius distance b. Note that in the present embodiment, the following form is preferably employed. Of the base end portion 47 of the coil spring unit CU, the position 41A (see FIG. 4) at a base end of the coil spring sleeve 41 is retained at the third radial position P3 by the coil spring contact portion 58.

With the above-described configuration, the retained portion 51 on the tip end side with respect to the base end portion 47 of the coil spring unit CU is, according to the endoscope 10 and the hardness adjustment device of the present embodiment, retained at the first radial position P1 by the coil spring holder 60 as the first retainer in the operation portion 12, and the base end portion 49 of the wire unit WU is retained at the second radial position P2 by the wire holder 52 as the second retainer. Thus, an internal space of the operation portion 12 can be effectively utilized. This can ensure an arrangement space of the built-in components in the operation portion 12.

Moreover, the base end portion 47 of the coil spring unit CU is retained at the third radial position P3 by the coil spring contact portion 58 as the third retainer. This can prevent the coil spring 40 from sharply bending in the operation portion 12 in compression operation of the coil spring 40. Further, the angle of bending of the wire 42 in the operation portion 12 is decreased. Thus, burden on the coil spring 40 and the wire 42 can be reduced.

In the present embodiment, the radial direction A and the radial direction B are preferably set to the same direction. This can allow arrangement of the coil spring 40 and the wire 42 in alignment with each other in the radial direction of the operation portion 12, and therefore, the burden on the coil spring 40 and the wire 42 can be reduced. Note that the radial direction A and the radial direction B are not necessarily set to the same direction, and the radial direction B may be a direction containing the component of the radial direction A.

In the coil compression type hardness adjustment device of the present embodiment, Expression (3) as described later is preferably satisfied:

$$(L3/L1) \times R1 \leq R2 \leq (L2/L1) \times R1 \qquad (3)$$

where the distance in the longitudinal direction from the retained portion 51 to the base end portion 49 of the wire unit WU is "L1," the distance in the longitudinal direction from the retained portion 51 to the base end portion 47 of the coil spring unit CU when the coil spring contact portion 58 is at a middle position of a movable area in the longitudinal direction is "L2," the distance in the longitudinal direction from the retained portion 51 to the base end portion 47 of the coil spring unit CU when the coil spring contact portion 58 is at a tip end position of the movable area in the longitudinal direction is "L3," the distance in the radial direction about the central axis X from the retained portion 51 to the base end portion 49 of the wire unit WU is "R1," and the distance in the radial direction about the central axis X from the retained portion 51 to the base end portion 47 of the coil spring unit CU is "R2."

When Expression (3) is not satisfied, the angle of bending of the wire 42 and the coil spring 40 is, as compared to the case of satisfying Expression (3), higher in hardness adjustment for increasing the hardness of the flexible portion 18, leading to the burden on the wire 42 and the coil spring 40.

The coil compression type hardness adjustment device of the present embodiment satisfies Expression (3), and therefore, the angle of bending of the wire 42 and the coil spring 40 can be decreased in hardness adjustment for increasing the hardness of the flexible portion 18. Thus, the burden on the wire 42 and the coil spring 40 can be further reduced.

Of the base end portion 49 of the wire unit WU, the position (the wire position) 42A of the wire at the tip end of the wire sleeve 50 is more preferably retained at the second radial position P2 by the wire holder 52 as the second retainer in the present embodiment. That is, in the case of the coil compression method of FIG. 11, the wire position 42A is preferably a position specifying the base end portion 49 of the wire unit WU to define L1 and R1 of Expression (3).

Of the base end portion 47 of the coil spring unit CU, the position (the sleeve position) 41A at the base end of the coil spring sleeve 41 is more preferably retained at the third radial position P3 by the coil spring contact portion 58 as the third retainer in the present embodiment. That is, in the case of the coil compression method of FIG. 11, the sleeve position 41A is preferably a position specifying the base end portion 47 of the coil spring unit CU to define L2, L3, and R2 of Expression (3).

Figure 12:
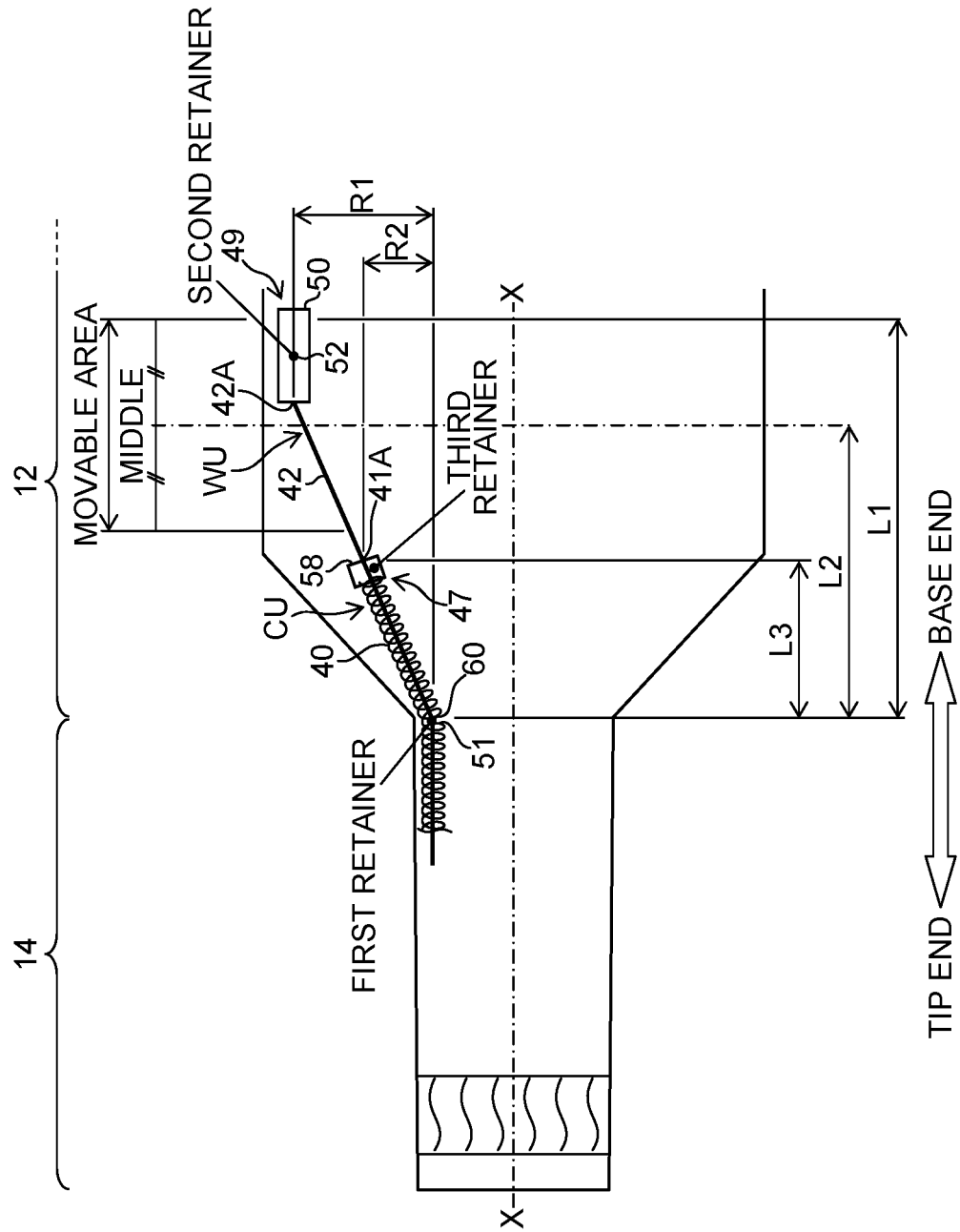
FIG. 12 is a view for describing a wire traction method, and illustrates the arrangement positions of the coil spring holder, the wire holder, and the coil spring contact portion in the longitudinal direction of the operation portion.

FIG. 12 is a view for describing the wire traction method, and illustrates the arrangement positions of the coil spring holder 60, the wire holder 52, and the coil spring contact portion 58 in the longitudinal direction of the operation portion 12.

Note that the wire traction method is a method by which the coil spring holder 60 and the coil spring contact portion 58 are fixed relative to the operation portion 12 and the wire holder 52 is movable relative to the operation portion 12 in the longitudinal direction.

In the case of the wire traction type hardness adjustment device, Expression (4) as described below is preferably satisfied:

$$(L2/L3) \times R2 \leq R1 \leq (L1/L3) \times R2 \qquad (4)$$

where the distance in the longitudinal direction from the retained portion 51 to the base end portion 49 of the wire unit WU when the wire holder 52 is at a base end position of a movable area in the longitudinal direction is "L1," the distance in the longitudinal direction from the retained portion 51 to the base end portion 49 of the wire unit WU when the wire holder 52 is at a middle position of the movable area in the longitudinal direction is "L2," the distance in the longitudinal direction from the retained portion 51 to the base end portion 47 of the coil spring unit CU is "L3," the distance in the radial direction about the central axis X from the retained portion 51 to the base end portion 49 of the wire unit WU is "R1," and the distance in the radial direction about the central axis X from the retained portion 51 to the base end portion 47 of the coil spring unit CU is "R2."

When Expression (4) is not satisfied, the angle of bending of the wire 42 and the coil spring 40 is, as compared to the case of satisfying Expression (4), higher in hardness adjustment for increasing the hardness of the flexible portion 18, leading to the burden on the wire 42 and the coil spring 40.

The wire traction type hardness adjustment device of the present embodiment satisfies Expression (4), and therefore, the angle of bending of the wire 42 and the coil spring 40 can be decreased in hardness adjustment for increasing the hardness of the flexible portion 18. Thus, the burden on the wire 42 and the coil spring 40 can be further reduced.

Of the base end portion 49 of the wire unit WU, the position (the wire position) 42A of the wire at the tip end of the wire sleeve 50 is, in the case of the wire traction method illustrated in FIG. 12, preferably a position specifying the base end portion 49 of the wire unit WU to define L1, L2, and R1 of Expression (4). Of the base end portion 47 of the coil spring unit CU, the position (the sleeve position) 41A at the base end of the coil spring sleeve 41 is preferably a position specifying the base end portion 47 of the coil spring unit CU to define L3 and R2 of Expression (4).

<Disclosure of Other Aspects of the Invention>
<<Shape of Operation Ring 36>>

As illustrated in FIGS. 6A and 6B, the operation ring 36 is provided on the outside of the cam ring 38 to rotate the cam ring 38, and the keys 36A of the operation ring 36 engage respectively with the key grooves 38A of the cam ring 38 to transmit rotation force of the operation ring 36 to the cam ring 38.

During endoscopic examination, the practitioner often operates the operation ring 36 with one's hand being wet. Thus, anti-slip processing is generally performed for the operation ring 36.

In the typical anti-slip processing for the operation ring, a shape with knurled portions or many fine grooves is generally employed as described in Japanese Patent Application Laid-Open No. 2002-253476. However, since such a shape has the fine grooves, contaminants tend to be accumulated on a bottom portion of each groove, and therefore, time and effort are involved in washing and sterilization. Moreover, a larger size of the operation ring results in easier transmission of operation force, but the operation ring is hard to be grasped when the operation ring is extremely large. Further, the operation ring rotates with slight operation force, leading to a problem that operation becomes difficult.

Figure 13C:
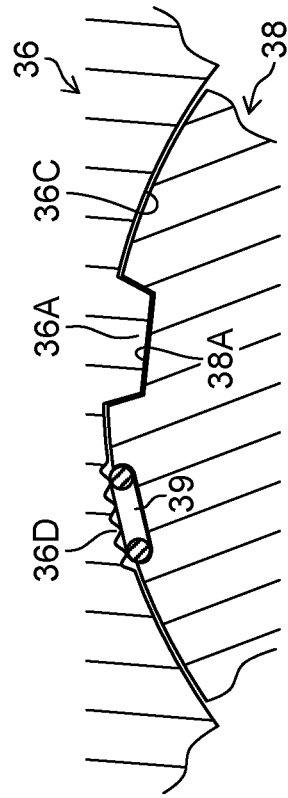
FIG. 13C is a front view of the operation ring.
Figure 13E:
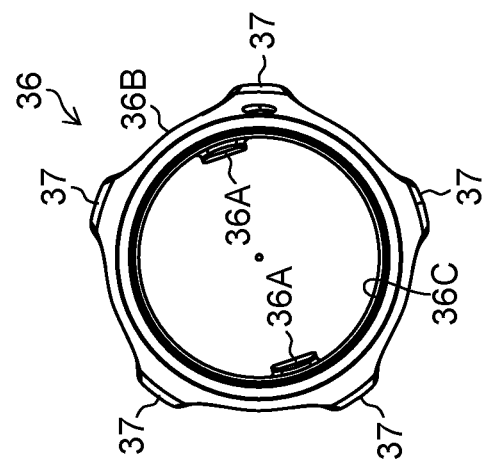
FIG. 13E is an enlarged view of a main portion of an engagement portion between the operation ring and the cam ring.
Figure 13B:
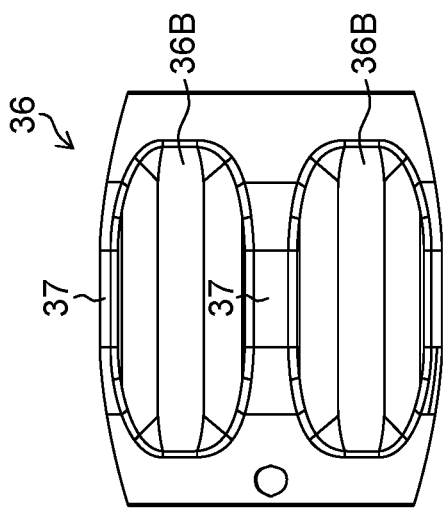
FIG. 13B is a side view of the operation ring.
Figure 13D:
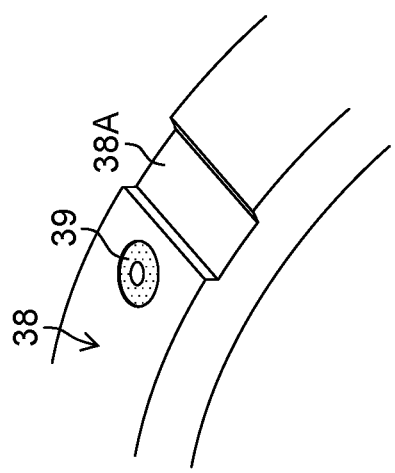
FIG. 13D is an enlarged perspective view of a main portion of the cam ring.
Figure 13A:
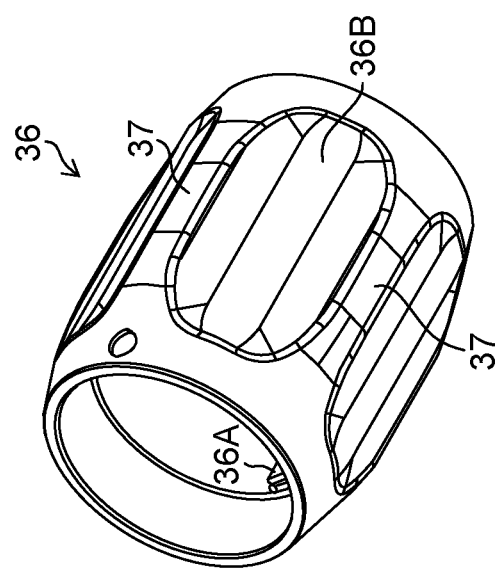
FIG. 13A is a perspective view of the operation ring.

FIG. 13A is a perspective view of the operation ring 36 of the present embodiment, FIG. 13B is a side view of the operation ring 36, FIG. 13C is a front view of the operation ring 36, FIG. 13D is an enlarged perspective view of a main portion of the cam ring 38, and FIG. 13E is an enlarged view of a main portion of an engagement portion between the operation ring 36 and the cam ring 38.

In order to solve the above-described problems, the operation ring 36 of the present embodiment is configured such that the number of anti-slip protrusions 37 of an outer peripheral surface 36B of the operation ring 36 is equal to or greater than three and equal to or lower than five. In FIGS. 13A to 13E, five protrusions 37 are provided at equal interval in the circumferential direction on the outer peripheral surface 36B. Moreover, the protrusions 37 and the outer peripheral surface 36B are connected together to define a smooth curved surface. Further, a value obtained by division of the maximum torque required for operation of the operation ring 36 by the radius of the outer peripheral surface 36B is equal to or greater than 50 N and equal to or less than 60 N. In addition, a difference in radius between each protrusion 37 and the outer peripheral surface 36B is equal to or greater than 1.5 mm and equal to or less than 3 mm.

With this configuration, the operation ring 36 of the hardness adjuster 34 easily operated by the practitioner and easily washed and sterilized can be provided.

As illustrated in FIG. 13D, an O-ring 39 is preferably embedded at a position adjacent to the key groove 38A on the outer peripheral surface of the cam ring 38. Moreover, as illustrated in FIG. 13E, a recessed-raised portion 36D is preferably formed at a position adjacent to the key 36A on an inner peripheral surface 36C of the operation ring 36. As illustrated in FIG. 13E, the O-ring 39 contacts the recessed-raised portion 36D of the operation ring 36. This generates great sliding resistance between the O-ring 39 and the recessed-raised portion 36D. Thus, noise caused by contact among the keys 36A and the key grooves 38A due to a clearance among the keys 36A and the key grooves 38A can be reduced.

<<Connection Structure between Relay Metal Fitting 44 and Coil Spring 46 as Cushion Member>>

Figure 14:
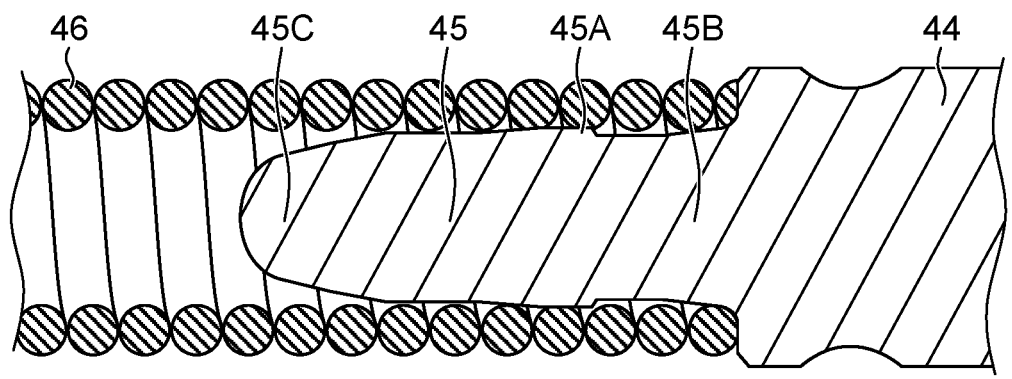
FIG. 14 is an enlarged longitudinal sectional view of a main portion of a connection structure between a coil spring and a relay metal fitting.

FIG. 14 is an enlarged longitudinal sectional view of a main portion of a connection structure between the relay metal fitting 44 and the coil spring 46.

The tip end portion of the relay metal fitting 44 is provided with a protrusion 45 protruding in the axial direction of the relay metal fitting 44. The entire length of the protrusion 45 is inserted into the base end portion of the coil spring 46, and in this manner, the relay metal fitting 44 and the coil spring 46 are connected together.

A middle portion of the protrusion 45 in the axial direction thereof is provided with a raised portion 45A extending in the circumferential direction of the protrusion 45 and caught by a wire of the coil spring 46. Moreover, a base end portion 45B and a tip end portion 45C divided with respect to the raised portion 45A form a non-fitting portion having a smaller diameter than the inner diameter of the coil spring 46. Further, the tip end portion 45C is formed in such a conical shape that the diameter thereof gradually decreases toward a tip end of the tip end portion 45C.

The connection structure illustrated in FIG. 14 is intended to prevent damage of the coil spring 46 due to repeated bending and curving of the coil spring 46.

Thus, the raised portion 45A is provided at a middle portion of a connection area where the relay metal fitting 44 and the coil spring 46 overlap with each other in the axial direction, and the curvature radius R of the curved coil spring 46 increases such that the coil spring 46 positioned on the tip end side with respect to the raised portion 45A is curved along a curved surface of the tip end portion 45C.

Figure 15:
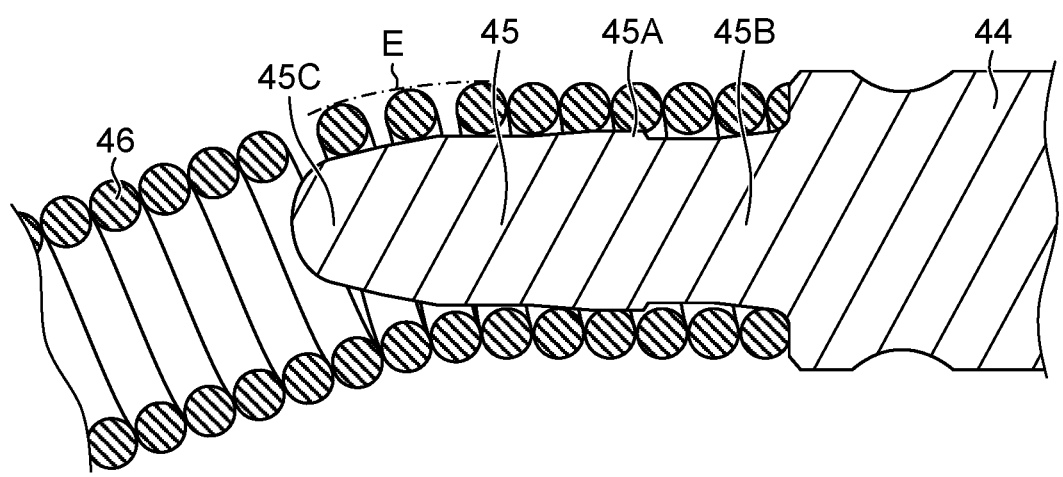
FIG. 15 is a view for describing the connection structure between the relay metal fitting and the coil spring in the state in which a hardness is maximum in a hardness variable by the hardness adjustment unit and the flexible portion is curved with the minimum curvature radius.

FIG. 15 is an enlarged longitudinal sectional view of a main portion of the connection structure in the state in which the hardness is maximum in a hardness variable by the hardness adjustment unit 32 and the flexible portion 18 is curved with the minimum curvature radius.

In the state of FIG. 15, the minimum curvature radius R formed by an envelope E on an outer base end side of the coil spring 46 is set within an elastic deformation range of the coil spring 46. In this case, the radius of the wire of the coil spring 46 is preferably less than the radius of a wire of the coil spring 40.

<<Structures of First Cam Pin 68 and First Cam Groove 78>>

In the hardness adjuster 34, the hardness of the flexible portion 18 is adjusted by compression of the coil spring 40 or traction of the wire 42, and therefore, the present embodiment discloses, as a mechanism for such hardness adjustment, a movement mechanism configured such that each first cam pin 68 engages with a corresponding one of the first cam grooves 78 as illustrated in FIG. 7.

When the cam ring 38 rotates through the operation ring 36 provided at the operation portion 12, each first cam pin 68 engaging with a corresponding one of the first cam grooves 78 moves back and forth in accordance with rotation of the cam ring 38. By forward movement of each first cam pin 68, compression force is applied to the base end portion 47 of the coil spring unit CU.

A load equivalent to the compression force on the coil spring 40 is applied to the surface of the first cam groove 78 and the outer peripheral surface of the first cam pin 68 contacting such a surface of the first cam groove 78. Such a load increases with an increase in hardness. On the other hand, the width of the first cam groove 78 and the outer diameter of the first cam pin 68 tend to decrease with a decrease in the size of the hardness adjuster 34. Thus, surface pressure on the surface of the first cam groove 78 and the outer peripheral surface of the first cam pin 68 is extremely high.

When each first cam pin 68 is, in the extremely-high surface pressure state, relatively operated along a corresponding one of the first cam grooves 78, the surface of the first cam groove 78 and the outer peripheral surface of the first cam pin 68 are abraded early, leading to a problem that operation becomes slow.

With the following structures of the cam ring 38 and the first cam pins 68 of the present embodiment, the above-described problems are solved.

That is, surface processing is preferably performed for at least one of the outer peripheral surface of each first cam pin 68 and the surface of each first cam groove 78 of the cam ring 38 to increase the surface hardness of at least one of these surfaces.

Specifically, the cam ring 38 and the first cam pins 68 are each made of a metal material such as stainless alloy (typically, SUS303). The stainless alloy is often used for an endoscope because of rust resistance of the stainless alloy. However, the stainless alloy has a low hardness, and galling/abrasion of the stainless alloy tends to be caused. For these reasons, the surface processing for increasing the surface hardness is performed for at least one of the cam ring 38 and the first cam pin 68. As a result, galling/abrasion is reduced, and resistance to a high load is exhibited.

The processing for improving the surface hardness by nitriding or plating is preferable as the type of surface processing. In particular, nitriding increases even the hardness in a relatively-deep portion of a base material, and therefore, provides an effect of preventing local deformation of each first cam groove 78 in the case of an extremely-high load. In addition, the processing not only for improving the surface hardness but also for reducing a friction coefficient is preferably applied.

Further, the surface hardness of the cam ring 38 and the surface hardness of each first cam pin 68 are not necessarily identical to each other, and it is preferable that there is a difference in surface hardness between the cam ring 38 and each first cam pin 68. It is effective to use different materials, but the above-described difference can be provided by the presence or absence of the surface processing.

Specifically, in the case of performing the surface processing, the surface hardness of each first cam groove 78 is preferably increased. Since the first cam groove 78 generally has a complicated structure with high cost as compared to the first cam pin 68, the first cam pin 68 is preferably abraded in advance of the first cam groove 78.

Further, it is also effective to increase the hardness by quenching of at least one of the above-described surfaces.

The structure for connecting each first cam pin 68 to the movable ring 56 is preferably a structure in which each first cam pin 68 of FIG. 4 is rotatably attached to a corresponding one of the pin holes 70 of the movable ring 56. Specifically, the structure for connecting each first cam pin 68 to the movable ring 56 is a fitting structure in which a clearance is formed between the pin hole 70 and the first cam pin 68 such that the first cam pin 68 is rotatable in the clearance. Each first cam pin 68 is retained at the axial position by the operation ring 36, the large-diameter portion 88, etc. fitted onto the first cam pins 68 (see FIGS. 9A and 9B). With such a structure, each first cam pin 68 receives a load by rolling of the first cam pin 68 itself, and therefore, the degree of abrasion can be greatly lowered. Even not in the case of combination for constant rolling, an abrasion surface is not fixed, and therefore, the degree of abrasion of the first cam pin 68 can be lowered.

Figure 16A:
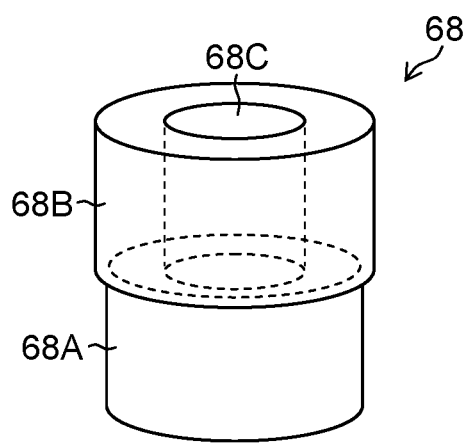
FIG. 16A is a view for describing a first cam pin divided into two portions.

As in the first cam pin 68 of FIG. 16A, each first cam pin 68 may include, as another form, two components of a shaft 68A and a ring 68B, and the ring 68B may be rotatably fitted onto a small-diameter portion 68C of the shaft 68A so that the ring 68B can be rotatably supported on the shaft 68A. The shaft 68A may be rotatably fitted into the pin hole 70, or may be fixed to the pin hole 70. Moreover, the shaft 68A and the ring 68B are preferably made of different materials. The shaft 68A is preferably made of a high-strength material such as stainless alloy having resistance to high shear force. The ring 68B is preferably made of, e.g., a sintered material or an oil-containing material having resistance to a high load and a small friction coefficient.

Lubricant is preferably applied to each first cam pin 68 such that rotary operation of the first cam pin 68 is smoothly performed. The lubricant preferably has favorable extreme pressure properties, and preferably contains a molybdenum compound.

Figure 16B:
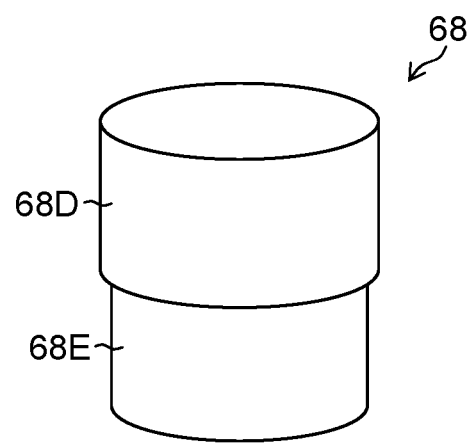
FIG. 16B is a view for describing a two-tiered first cam pin.

FIG. 16B is a view for describing still another form of the first cam pin 68.

Each first cam pin 68 has two levels of outer diameter. The first cam pin 68 is configured such that a portion 68D contacting the surface of the first cam groove 78 has a slightly-larger diameter, and a portion 68E fitted into the pin hole 70 has a slightly-smaller diameter. This can prevent the first cam pin 68 from dropping into the movable ring 56.

When the first ring 84 and the second ring 86 are connected together as illustrated in FIG. 10B, the first cam grooves 78 of the first ring 84 are covered with the large-diameter portion 88 of the second ring 86, and therefore, dropping of the first cam pins 68 to the outside is prevented.

A head portion of each first cam pin 68 is preferably provided with a small-diameter hole. Thus, the first cam pin 68 can be easily grasped with, e.g., tweezers. In addition, it is also effective to improve workability by the following method: each first cam pin 68 is made of a magnetic material so that the first cam pin 68 can be detached using a magnetic tool.

According to the first cam pins 68 and the first cam grooves 78 with the above-described configuration, rotary operation can be smoothly performed, and functions and a quality can be maintained even after repeated use.

<<Stopper Structure for First Cam Pin 68>>

An anti-dropping member configured to prevent each first cam pin 68 from dropping from a corresponding one of the pin holes 70 to the outside is preferably provided on the outside of the cam ring 38.

The configuration in which the outer periphery of each first cam groove 78 is covered with the large-diameter portion 88 of the second ring 86 illustrated in FIGS. 9A and 9B can prevent, as an example, each first cam pin 68 from dropping from a corresponding one of the pin holes 70 to the outside.

Figure 17:
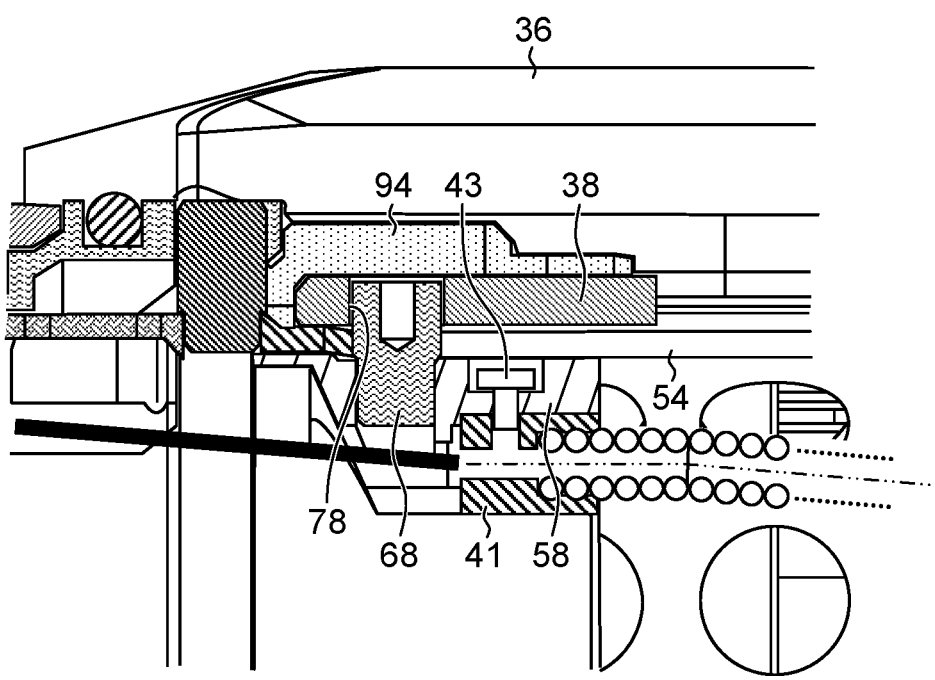
FIG. 17 is an enlarged longitudinal sectional view of a main portion of an anti-dropping member of a first embodiment.

FIG. 17 is an enlarged longitudinal sectional view of a main portion of an anti-dropping member 94 of a first embodiment.

The anti-dropping member 94 covering the outer periphery of each first cam groove 78 is formed in a ring shape, and is attached to the outside of the cam ring 38. Examples of an attachment method include a method in which an external thread formed at the outer peripheral surface of the cam ring 38 and an internal thread formed at an inner peripheral surface of the anti-dropping member are coupled together by screwing.

Figure 18:
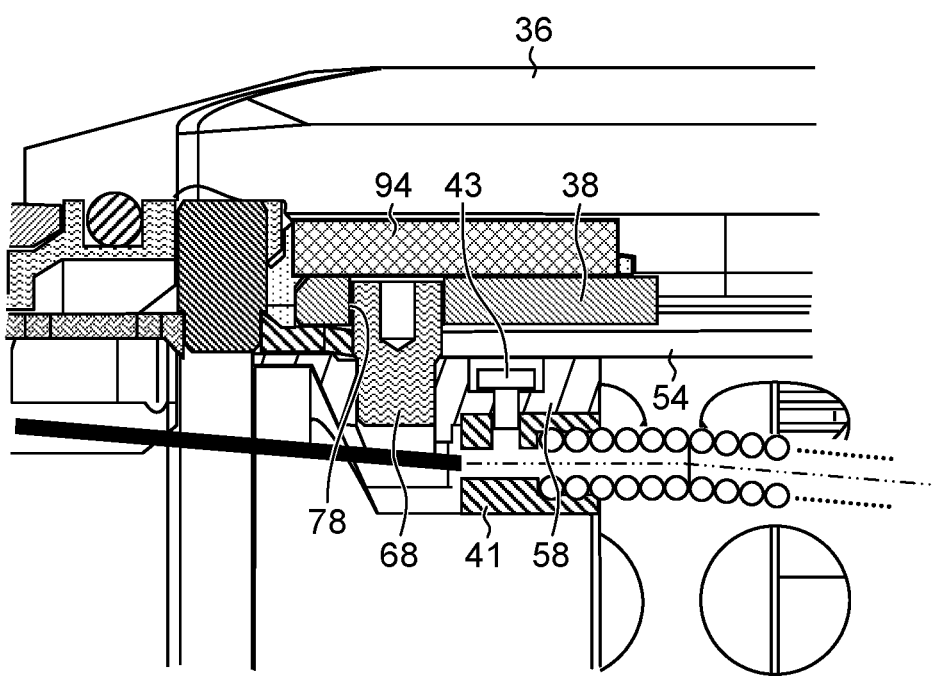
FIG. 18 is an enlarged longitudinal sectional view of a main portion of an anti-dropping member of a second embodiment.

FIG. 18 is an enlarged longitudinal sectional view of a main portion of an anti-dropping member 96 of a second embodiment.

The anti-dropping member 96 covering the outer periphery of each first cam groove 78 is made of sheet metal, and is fixed to the outer peripheral surface of the cam ring 38 with a screw or an adhesive.

Figure 19:
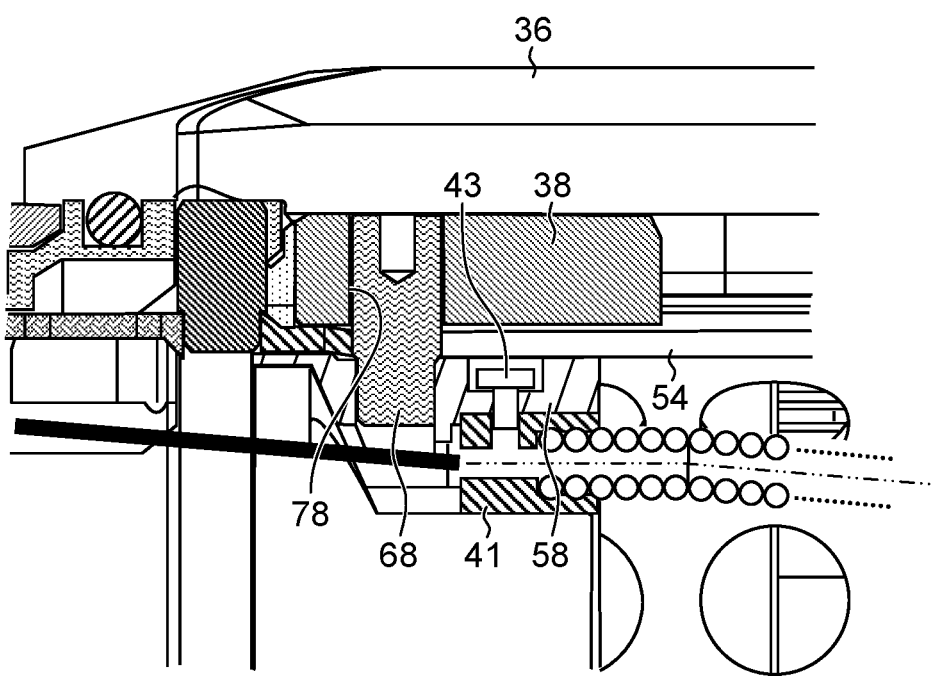
FIG. 19 is an enlarged longitudinal sectional view of a main portion of an anti-dropping member of a third embodiment.

FIG. 19 is an enlarged longitudinal sectional view of a main portion of an anti-dropping member of a third embodiment.

A clearance between the outer peripheral surface of the cam ring 38 and the inner peripheral surface of the operation ring 36 is formed narrower than a stroke length causing dropping of the first cam pin 68, and therefore, the operation ring 36 functions as the anti-dropping member. That is, the thickness of the cam ring 38 is increased in the direction toward the operation ring 36, and therefore, the cam ring 38 can function as the anti-dropping member.

<<Anti-Rotation Structure for Wire 42>>

The wire of the coil spring 40 formed in such a manner that the wire is wound in a spiral shape receives torsion force in the direction opposite to a winding direction of the wire. That is, the wire receives force in the direction in which the number of turns of the wire decreases. For this reason, the axial natural length of the coil spring 40 is shortened due to such force, leading to a problem that durability of the coil spring 40 is lowered.

In order to solve the above-described problem, rotation of the wire 42 is, in the present embodiment, restricted to solve the above-described problem. Specifically, as illustrated in FIG. 4, the wire sleeve 50 forming the base end portion 49 of the wire unit WU is held with rotation of the wire sleeve 50 relative to the wire holder 52 being restricted.

That is, the force, which is received by the wire of the coil spring 40, in the direction in which the number of turns of the wire decreases is received by the wire 42 fixed to the tip end portion of the coil spring 40 through the relay metal fitting 44, and therefore, shortening of the natural length of the coil spring 40 is prevented.

Figure 20:
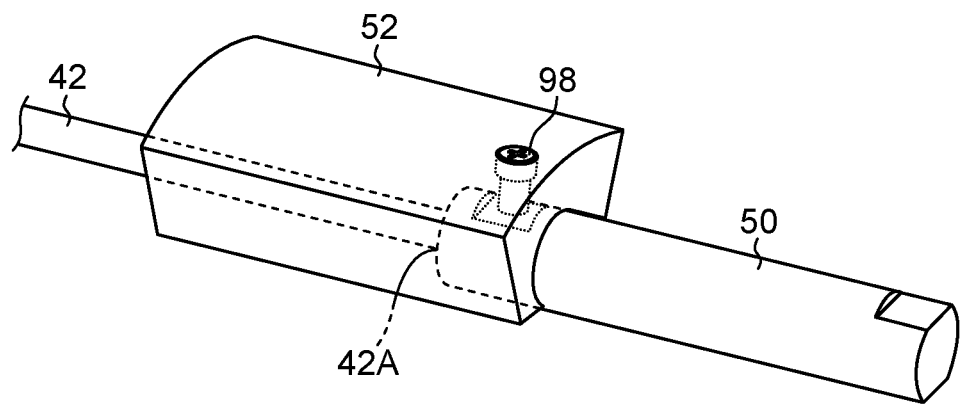
FIG. 20 is an enlarged view of a main portion of an anti-rotation structure for a wire.

FIG. 20 is an enlarged view of a main portion of an anti-rotation structure for the wire 42.

According to FIG. 20, a tip end portion of the wire sleeve 50 forming the base end portion 49 of the wire unit WU is fastened to the wire holder 52 by a screw 98, and in this manner, rotation of the wire 42 is restricted.

In this case, the winding direction of the wire of the wire 42 and the winding direction of the wire of the coil spring 40 are preferably opposite to each other.

Moreover, the torsional rigidity of the wire of the wire 42 is preferably higher than that of the wire of the coil spring 40. This is because of the following reason: in the reverse case, when the movable ring 56 moves forward to compress the coil spring 40, torsion is caused at the wire 42, and for this reason, does not return to an original shape. That is, kink is caused at the wire 42.

What is claimed is:

1. An endoscope comprising:
   an insertion portion including a flexible portion;
   an operation portion provided continuously to a base end side of the insertion portion;
   a coil spring unit including a coil spring provided to extend from the flexible portion to the operation portion;
   a wire unit provided to extend from the flexible portion to the operation portion and including a wire inserted into the coil spring and fixed to a tip end portion of the coil spring; and a hardness adjuster provided at the operation portion and configured to adjust a hardness of the flexible portion in such a manner that the coil spring is compressed with a base end of the coil spring and a base end of the wire being apart from each other, wherein the hardness adjuster includes
- a wire holder configured to hold a base end portion of the wire unit protruding toward the base end side beyond a base end portion of the coil spring unit,
- a coil spring contact portion contacting the base end portion of the coil spring unit,
- a relative distance changer configured to change a distance in a longitudinal direction of the operation portion between the coil spring contact portion and the wire holder, and
- a retainer configured to retain a retained portion at a first radial position apart from a center axis of the operation portion along the longitudinal direction by a first radius distance, the retained portion being positioned on a tip end side with respect to the base end portion of the coil spring unit, wherein
  the wire holder is configured to retain the base end portion of the wire unit at a second radial position apart from the center axis in a radial direction A by a second radius distance longer than the first radius distance, the base end portion of the wire unit being held by the wire holder, and
  the coil spring contact portion is configured to retain the base end portion of the coil spring unit at a third radial position apart from the center axis in a radial direction B having a component of the radial direction A by a third radius distance longer than the first radius distance and shorter than the second radius distance, the base end portion of the coil spring unit contacting the coil spring contact portion.

2. The endoscope according to claim 1, wherein the radial direction A and the radial direction B are identical to each other.

3. The endoscope according to claim 1, wherein the wire holder is fixed relative to the operation portion, and the coil spring contact portion is movable relative to the operation portion in the longitudinal direction.

4. The endoscope according to claim 2, wherein the wire holder is fixed relative to the operation portion, and the coil spring contact portion is movable relative to the operation portion in the longitudinal direction.

5. The endoscope according to claim 3, wherein a following expression is satisfied:

$$(L3/L1) \times R1 \leq R2 \leq (L2/L1) \times R1,$$

where a distance in the longitudinal direction from the retained portion to the base end portion of the wire unit is L1, a distance in the longitudinal direction from the retained portion to the base end portion of the coil spring unit when the coil spring contact portion is at a middle position of a movable area in the longitudinal direction is L2, a distance in the longitudinal direction from the retained portion to the base end portion of the coil spring unit when the coil spring contact portion is at a tip end position of the movable area in the longitudinal direction is L3, a distance in the radial direction about the central axis from the retained portion to the base end portion of the wire unit is R1, and a distance in the radial direction about the central axis from the retained portion to the base end portion of the coil spring unit is R2.

6. The endoscope according to claim 4, wherein a following expression is satisfied:

$$(L3/L1) \times R1 \leq R2 \leq (L2/L1) \times R1,$$

where a distance in the longitudinal direction from the retained portion to the base end portion of the wire unit is L1, a distance in the longitudinal direction from the retained portion to the base end portion of the coil spring unit when the coil spring contact portion is at a middle position of a movable area in the longitudinal direction is L2, a distance in the longitudinal direction from the retained portion to the base end portion of the coil spring unit when the coil spring contact portion is at a tip end position of the movable area in the longitudinal direction is L3, a distance in the radial direction about the central axis from the retained portion to the base end portion of the wire unit is R1, and a distance in the radial direction about the central axis from the retained portion to the base end portion of the coil spring unit is R2.

7. The endoscope according to claim 1, wherein the coil spring contact portion is fixed relative to the operation portion, and the wire holder is movable relative to the operation portion in the longitudinal direction.

8. The endoscope according to claim 2, wherein the coil spring contact portion is fixed relative to the operation portion, and the wire holder is movable relative to the operation portion in the longitudinal direction.

9. The endoscope according to claim 7, wherein a following expression is satisfied:

$$(L2/L3) \times R2 \leq R1 \leq (L1/L3) \times R2,$$

where a distance in the longitudinal direction from the retained portion to the base end portion of the wire unit when the wire holder is at a base end position of a movable area in the longitudinal direction is L1, a distance in the longitudinal direction from the retained portion to the base end portion of the wire unit when the wire holder is at a middle position of the movable area in the longitudinal direction is L2, a distance in the longitudinal direction from the retained portion to the base end portion of the coil spring unit is L3, a distance in the radial direction about the central axis from the retained portion to the base end portion of the wire unit is R1, and a distance in the radial direction about the central axis from the retained portion to the base end portion of the coil spring unit is R2.

10. The endoscope according to claim 8, wherein a following expression is satisfied:

$$(L2/L3) \times R2 \leq R1 \leq (L1/L3) \times R2,$$

where a distance in the longitudinal direction from the retained portion to the base end portion of the wire unit when the wire holder is at a base end position of a movable area in the longitudinal direction is L1, a distance in the longitudinal direction from the retained portion to the base end portion of the wire unit when the wire holder is at a middle position of the movable area in the longitudinal direction is L2, a distance in the longitudinal direction from the retained portion to the base end portion of the coil spring unit is L3, a distance in the radial direction about the central axis from the retained portion to the base end portion of the wire unit is R1, and a distance in the radial direction about the central axis from the retained portion to the base end portion of the coil spring unit is R2.

11. The endoscope according to claim 1, wherein
the wire unit includes a wire sleeve attached to a base end portion of the wire, and
the base end portion of the wire unit is configured to include the wire sleeve.

12. The endoscope according to claim 1, wherein
the coil spring unit includes a coil spring sleeve attached to a base end portion of the coil spring, and
the base end portion of the coil spring unit is configured to include the coil spring sleeve.

13. A hardness adjustment device provided at an endoscope including an insertion portion having a flexible portion and an operation portion provided continuously to a base end side of the insertion portion, comprising:
   a coil spring unit including a coil spring provided to extend from the flexible portion to the operation portion;
   a wire unit provided to extend from the flexible portion to the operation portion and including a wire inserted into the coil spring and fixed to a tip end portion of the coil spring; and
   a hardness adjuster provided at the operation portion and configured to adjust a hardness of the flexible portion in such a manner that the coil spring is compressed with a base end of the coil spring and a base end of the wire being apart from each other,
   wherein the hardness adjuster includes
      a wire holder configured to hold a base end portion of the wire unit protruding toward the base end side beyond a base end portion of the coil spring unit,
      a coil spring contact portion contacting the base end portion of the coil spring unit,
      a relative distance changer configured to change a distance in a longitudinal direction of the operation portion between the coil spring contact portion and the wire holder, and
      a retainer configured to retain a retained portion at a first radial position apart from a center axis of the operation portion along the longitudinal direction by a first radius distance, the retained portion being positioned on a tip end side with respect to the base end portion of the coil spring unit, wherein
   the wire holder is configured to retain the base end portion of the wire unit at a second radial position apart from the center axis in a radial direction A by a second radius distance longer than the first radius distance, the base end portion of the wire unit being held by the wire holder, and
   the coil spring contact portion is configured to retain the base end portion of the coil spring unit at a third radial position apart from the center axis in a radial direction B having a component of the radial direction A by a third radius distance longer than the first radius distance and shorter than the second radius distance, the base end portion of the coil spring unit contacting the coil spring contact portion.

* * * * *